(12) United States Patent
Raymond et al.

(10) Patent No.: US 11,857,259 B2
(45) Date of Patent: *Jan. 2, 2024

(54) APPARATUS AND METHOD FOR AUTOMATED NON-CONTACT EYE EXAMINATION

(71) Applicants: Thomas Daniel Raymond, Edgewood, NM (US); Stephen W Farrer, Albuquerque, NM (US)

(72) Inventors: Thomas Daniel Raymond, Edgewood, NM (US); Stephen W Farrer, Albuquerque, NM (US)

(73) Assignee: Scintellite, LLC, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/715,457

(22) Filed: Apr. 7, 2022

(65) Prior Publication Data

US 2022/0225876 A1   Jul. 21, 2022

Related U.S. Application Data

(63) Continuation of application No. 17/321,409, filed on May 15, 2021, now Pat. No. 11,324,400.
(Continued)

(51) Int. Cl.
*A61B 3/113* (2006.01)
*A61B 3/00* (2006.01)
(Continued)

(52) U.S. Cl.
CPC ............ *A61B 3/113* (2013.01); *A61B 3/0008* (2013.01); *A61B 3/0025* (2013.01);
(Continued)

(58) Field of Classification Search
CPC ..... A61B 3/113; A61B 3/0008; A61B 3/0025; A61B 3/0041; A61B 3/102; A61B 3/103;
(Continued)

(56) References Cited

U.S. PATENT DOCUMENTS 3,879,113 A   4/1975 Howland et al.
4,209,252 A   6/1980 Arditty et al.
(Continued)

FOREIGN PATENT DOCUMENTS

WO   WO2005077256 A1   8/2005
WO   WO2006061480 A1   6/2006
(Continued)

*Primary Examiner* — Mohammed A Hasan
(74) *Attorney, Agent, or Firm* — Springer Patents; Kenneth D. Springer

(57) ABSTRACT

An eye measurement system includes an optical system. The eye measurement system is disposed in a housing which includes an aperture for providing light to and from the optical system and a subject's eye while the subject is separated and spaced apart from the housing, and the eye is not maintained in a fixed positional relationship with respect to the housing. An optical system movement arrangement moves the optical system. An automatic eye tracking arrangement ascertains a current positional relationship of the eye with respect to the optical system without human assistance, and in response thereto controls the optical system movement arrangement to move the optical system into a predetermined positional relationship with respect to the eye, for measurement of the eye, without human assistance. The eye measurement system can make objective, and/or subjective, refraction measurements of the eye.

23 Claims, 22 Drawing Sheets

Related U.S. Application Data

(60) Provisional application No. 63/048,946, filed on Jul. 7, 2020.

(51) Int. Cl.
| | |
|---|---|
| *A61B 3/103* | (2006.01) |
| *G16H 40/67* | (2018.01) |
| *A61B 3/10* | (2006.01) |
| *A61B 3/12* | (2006.01) |
| *A61B 3/135* | (2006.01) |
| *A61B 3/16* | (2006.01) |

(52) U.S. Cl.
CPC ............ *A61B 3/0041* (2013.01); *A61B 3/102* (2013.01); *A61B 3/103* (2013.01); *A61B 3/12* (2013.01); *A61B 3/135* (2013.01); *A61B 3/16* (2013.01); *G16H 40/67* (2018.01)

(58) Field of Classification Search
CPC .. A61B 3/12; A61B 3/135; A61B 3/16; A61B 3/18; A61B 3/032; G16H 40/67; G16H 30/20; G16H 30/40; G16H 40/63
USPC ......................................................... 351/209
See application file for complete search history.

(56) References Cited

U.S. PATENT DOCUMENTS

| | | | |
|---|---|---|---|
| 4,834,527 A | 5/1989 | Kobayashi | |
| 5,094,521 A | 3/1992 | Jolson et al. | |
| 5,420,650 A | 5/1995 | Kohayakawa | |
| 5,532,769 A | 7/1996 | Miwa et al. | |
| 5,708,494 A | 1/1998 | Iijima et al. | |
| 6,309,068 B1 * | 10/2001 | Kohayakawa | A61B 3/028 351/221 |
| 6,361,167 B1 | 3/2002 | Su et al. | |
| 6,669,340 B2 | 12/2003 | Percival et al. | |
| 7,232,220 B2 | 6/2007 | Franz et al. | |
| 7,357,506 B2 | 4/2008 | Shimizu et al. | |
| 7,367,675 B2 | 5/2008 | Maddalena et al. | |
| 7,520,611 B2 | 4/2009 | Franz et al. | |
| 7,533,991 B2 | 5/2009 | Baumann et al. | |
| 7,588,336 B2 | 9/2009 | Honda et al. | |
| 7,631,970 B2 | 12/2009 | Wei | |
| 7,708,406 B2 | 5/2010 | Koest | |
| 7,818,041 B2 | 10/2010 | Kim et al. | |
| 7,840,418 B2 | 11/2010 | Shoenberg | |
| 7,909,462 B2 | 3/2011 | Takahashi et al. | |
| 8,123,353 B2 | 2/2012 | Biernat et al. | |
| 8,444,270 B2 | 5/2013 | Nordstrom | |
| 8,793,142 B2 | 7/2014 | Fishman et al. | |
| 9,173,563 B2 | 11/2015 | Buckland et al. | |
| 9,230,062 B2 | 1/2016 | Seriani | |
| 9,277,863 B2 | 3/2016 | Liang | |
| 9,301,675 B2 | 4/2016 | Kiderman et al. | |
| 9,380,934 B2 | 7/2016 | Sugiura et al. | |
| 9,504,378 B2 | 11/2016 | Lee et al. | |
| 9,730,578 B2 | 8/2017 | Lai | |
| 9,980,644 B2 | 5/2018 | Fried et al. | |
| 10,022,050 B2 | 7/2018 | Isogai | |
| 10,083,279 B2 | 9/2018 | Seriani | |
| 10,264,966 B2 | 4/2019 | Yamamoto et al. | |
| 10,524,658 B2 | 1/2020 | Fried et al. | |
| 10,583,039 B2 | 3/2020 | Raymond et al. | |
| 10,602,928 B2 | 3/2020 | Fried et al. | |
| 10,734,114 B2 | 8/2020 | Seriani | |
| 10,762,994 B2 | 9/2020 | Seriani | |
| 10,827,925 B2 | 11/2020 | Fried et al. | |
| 10,874,299 B2 | 12/2020 | Seriani | |
| 11,324,400 B2 * | 5/2022 | Raymond | A61B 3/0041 |
| 2003/0117580 A1 | 6/2003 | Franz et al. | |
| 2006/0026051 A1 | 2/2006 | Rose | |
| 2006/0084856 A1 | 4/2006 | Biggins et al. | |
| 2006/0290885 A1 | 12/2006 | Covannon et al. | |
| 2007/0171367 A1 | 7/2007 | Sebastian et al. | |
| 2007/0195267 A1 | 8/2007 | Franz et al. | |
| 2008/0284979 A1 * | 11/2008 | Yee | A61B 3/103 351/205 |
| 2009/0080712 A1 * | 3/2009 | D'Souza | G06V 20/52 382/117 |
| 2009/0153796 A1 * | 6/2009 | Rabner | A61B 3/024 351/203 |
| 2009/0228299 A1 | 9/2009 | Kangarloo et al. | |
| 2010/0097576 A1 | 4/2010 | Witt et al. | |
| 2011/0202017 A1 | 8/2011 | Reimer | |
| 2013/0100410 A1 | 4/2013 | Liang | |
| 2014/0126700 A1 | 5/2014 | Gertner et al. | |
| 2014/0129259 A1 | 5/2014 | Seriani | |
| 2016/0098528 A1 | 4/2016 | Seriani | |
| 2016/0128560 A1 | 5/2016 | Lee et al. | |
| 2016/0198943 A1 | 7/2016 | Lai | |
| 2016/0262617 A1 | 9/2016 | Gerrans | |
| 2016/0310000 A1 | 10/2016 | Meneghini | |
| 2016/0317025 A1 | 11/2016 | Lee et al. | |
| 2016/0338583 A1 | 11/2016 | Uchida | |
| 2017/0007111 A1 | 1/2017 | Samec et al. | |
| 2017/0027436 A1 | 2/2017 | Lee et al. | |
| 2017/0027444 A1 | 2/2017 | Rege et al. | |
| 2017/0027445 A1 | 2/2017 | Isogai | |
| 2017/0060399 A1 | 3/2017 | Hough et al. | |
| 2017/0061698 A1 | 3/2017 | Luebke et al. | |
| 2017/0100031 A1 | 4/2017 | Lai | |
| 2017/0135572 A1 | 5/2017 | Takii et al. | |
| 2017/0156591 A1 | 6/2017 | Berestka et al. | |
| 2017/0188811 A1 | 7/2017 | Lee | |
| 2017/0269358 A9 | 9/2017 | Luebke et al. | |
| 2017/0311796 A1 | 11/2017 | Walsh et al. | |
| 2017/0325675 A1 | 11/2017 | Liu et al. | |
| 2018/0070820 A1 | 3/2018 | Fried et al. | |
| 2018/0078134 A1 | 3/2018 | Katz et al. | |
| 2018/0092525 A1 | 4/2018 | Lai | |
| 2018/0192872 A1 | 7/2018 | Fried et al. | |
| 2019/0239790 A1 | 8/2019 | Gross et al. | |
| 2020/0029811 A1 | 1/2020 | Fried et al. | |
| 2020/0359891 A1 | 11/2020 | Fried et al. | |
| 2020/0405148 A1 | 12/2020 | Tran | |
| 2021/0011553 A1 | 1/2021 | Lussier et al. | |
| 2021/0015364 A1 | 1/2021 | Rege et al. | |
| 2021/0022603 A1 | 1/2021 | Predham et al. | |
| 2021/0051407 A1 | 2/2021 | Spector | |

FOREIGN PATENT DOCUMENTS

| | | |
|---|---|---|
| WO | WO2011034638 A1 | 3/2011 |
| WO | WO2013105915 A1 | 7/2013 |
| WO | WO2014074157 A1 | 5/2014 |

* cited by examiner

19000

Scintellite

Patient Information

Enter patient ID# [ ]

OR fill out the following information:

Patient Last Name * [ ]

Patient First Name * [ ]

Middle Initial [ ]

Date of Birth (DOB)* [ ] mm/dd/yyyy

One of the following is required for communication purposes only (see our privacy policy)

email * [ ]

cell * [ ] (include area code, 10 numbers only)

Submit ------------- Cancel

FIG.19

APPARATUS AND METHOD FOR AUTOMATED NON-CONTACT EYE EXAMINATION

CROSS-REFERENCE TO RELATED APPLICATION

This patent application is a continuation of U.S. patent application Ser. No. 17/321,409, filed on 15 May 2021, and claims priority under 35 U.S.C. § 119(e) from U.S. provisional patent application 63/048,946 filed on 7 Jul. 2020 in the name of Thomas D. Raymond et al., the entirety of each of which applications is hereby incorporated by reference herein as if fully set forth herein.

BACKGROUND

In 2019, only about half of the people in the United States completed their recommended annual vision examination for a variety of reasons including inconvenience, lack of transportation, lack of awareness of eye health issues, and the high cost of eyeglasses; this in spite of the fact that 93 million adults in the United States are at high risk of vision loss.

Similar trends are found internationally. In China, Japan, and Singapore less than one third of patients receive annual comprehensive eye exams despite the fact that an epidemic level of myopia progression in the Asia Pacific region poses a significant threat of visual impairment.

Furthermore, this rate may decline substantially in the future given the perceived risks of infection associated with routine eye examinations, especially in view of the worldwide COVID-19 pandemic and other possible future pandemics. Risks are present through hand, body, and facial contact with multiple ophthalmic instruments and chairs, and from the close proximity to technicians and to other subjects or patients in the waiting room.

During the pandemic, the American Academy of Ophthalmology and the American Society of Retina Specialists recommended ophthalmologists restrict seeing patients to urgent and emergency cases and to screen incoming patients for the novel coronavirus. In the eye clinic, multiple traditional ophthalmic instruments are used in an eye exam, each requiring patient contact and thorough decontamination between patients. Patient workflow is reduced by clinical floor space limitations that have driven most practices to tightly pack the necessary multiple instruments into small examination rooms that are inherently inconsistent with social distancing. The reduced patient workflow and the additional burden from implementing necessary protocols to see patients have added to an already overly burdened patient workflow and serve to increase stress on health care providers (HCPs).

Post-COVID-19 pressures will be significant on Health Care Providers (HCPs) as well. As the ratio of practitioners to patients diminishes, these practices will need to be ever more efficient to handle the increasing burden of eye care. These constraints immediately disqualify virtually all traditional single-purpose ophthalmic instruments and clearly beg for a new eye examination paradigm for this new era.

Fortunately, ophthalmology has been a national leader in telemedicine augmented by technology and artificial intelligence. On Mar. 30, 2020, the U.S. Centers for Medicare & Medicaid Services released temporary regulatory waivers and issued new rules for virtual visits using online applications for billable telemedical services. In an April 2020 survey of 1300 eye HCPs, 88% indicated that they already offer remote medical examinations, mostly through phone-based consultations, and 56% indicated that they had billed for telehealth services in the previous week.

However, existing telemedicine approaches can only capture a subset of the tests required for a full eye exam. For example, while visual acuity testing is possible without special equipment and can be used to verify a patient's current refractive prescription, without a refraction measurement it is not possible to alter that prescription or to provide a new patient a prescription. A refraction measurement typically requires refractive hardware and a skilled technician to operate it, hence tele-refraction is rarely available. For this reason, only 1.8% of those eye HCPs offer remote refractions. Finally, when asked "What would help you now?" the number one HCP response (64%) was "How to gear back up when re-opening."

Furthermore, even if/when the COVID-19 pandemic subsides, there will continue to be a need for unattended and/or remotely-controlled eye examination equipment, for example to meet the eyecare needs in third world and developing countries and in remote and rural areas where access to in-person treatment is difficult. Also, in the case of unattended remote kiosks, prevention or minimization of contamination of the equipment is especially important as there may be no one available to clean, decontaminate or sterilize the equipment with any frequency.

Accordingly, it would be desirable to provide a system and method for automated, non-contact, eye examination.

SUMMARY

As disclosed herein an apparatus comprises: a processing system including a user interface; an eye measurement system including an optical system, wherein the eye measurement system is configured to make at least one optical measurement of an eye of a subject; a housing having the eye measurement system disposed therein, wherein the housing includes an aperture for providing light to and from the optical system and the eye while the subject is separated and spaced apart from the housing and while the eye is not maintained in a fixed positional relationship with respect to the housing; an optical system movement arrangement which is configured to move the optical system; and an automatic eye tracking arrangement which is configured to ascertain a current positional relationship of the eye with respect to the optical system without human assistance, and in response thereto to control the optical system movement arrangement to move the optical system into a predetermined positional relationship with respect to the eye without human assistance. The eye measurement system includes: at least one objective refractive measurement device which is configured to make an objective refraction measurement of the eye via the optical system, a target, and a mirror system disposed in an optical path between the eye and the target for extending a length of the optical path, wherein the optical path further comprises at least one optical element of the optical system. The processing system is configured to interact with the subject via the user interface and in response to the interaction to adjust at least one parameter of the optical system to make a subjective refraction measurement of the eye based on the subject viewing the target.

In some embodiments, the housing conforms to 3A sanitary standards.

In some embodiments, the housing comprises an antimicrobial material disposed at an exterior surface thereof.

In some embodiments, the optical system movement arrangement is configured to move the optical system in two dimensions.

In some embodiments, the optical system movement arrangement is configured to move the optical system in three dimensions.

In some embodiments, the optical system includes a first lens, and the automatic eye tracking arrangement includes a Lidar device which is configured to provide light to the eye via the first lens and to receive returned light from the eye via the first lens for determining a distance between the eye and the first lens.

In some versions of these embodiments, the optical system includes a pre-compensation section which is configurable to bring the target into focus on the subject's eye for making the subjective refraction measurement of the subject's eye, and the distance between the eye and the first lens as determined by the Lidar device is employed to adjust a position of at least one lens in the pre-compensation section to maintain focus and refractive correction for the eye.

In some embodiments, the automatic eye tracking arrangement comprises: at least one light source configured to illuminate the eye; and at least one camera configured to receive an image of the eye, wherein the camera is configured to output image data of the image of the eye to the processing system, and wherein the processing system is configured to control the optical system movement arrangement to move the optical system into the predetermined positional relationship with respect to the eye based on the image data.

In some embodiments, the apparatus includes a communication device, wherein the communication device is configured to communicate eye measurement data from the apparatus to an external remote terminal for evaluation.

In some versions of these embodiments, the communication device is configured to communicate the eye measurement data from the apparatus to the external remote terminal via the Internet.

In some versions of these embodiments, the processing system is configured to execute a filtration algorithm for filtering the eye measurement data prior to communication to the external remote terminal to reject at least a portion of the eye measurement data when the portion of the eye measurement data is taken when the automatic eye tracking arrangement has not aligned the optical system to the eye within a specified level of accuracy.

In some versions of these embodiments, the apparatus, further comprises: at least one light source configured to illuminate the eye; and at least one camera configured to capture images of the eye, wherein the processing system is configured to execute a filtration algorithm for filtering the eye measurement data prior to communication to the external remote terminal to reject at least a portion of the eye measurement data when the portion of the eye measurement data is taken when the images of the eye fail to meet predefined quality criteria due to at least one of: a full blink, a partial blink, an incorrect gaze angle, incomplete disaccommodation, and a saccade.

In some embodiments, the optical system includes a pre-compensation section which is configurable to bring the target into focus on the subject's eye for making the subjective refraction measurement of the subject's eye.

In some versions of these embodiments, the pre-compensation section comprises one of: a set of discrete lenses, a Badal Optometer, Badal Optometer with Stokes cell, a variable focal length lens, a phase-only spatial light modulator, a deformable mirror and a retroreflection refractometer.

In some versions of these embodiments, the pre-compensation section comprises the phase-only spatial light modulator, and the phase-only spatial light modulator is configured to compensate for tilt which is introduced by head and eye motion by the subject.

In some embodiments, the at least one objective refractive measurement device includes one of: a Shack-Hartmann wavefront detector, a phase diversity sensor, a pyramid sensor, a curvature sensor, a point spread function (PSF) sensor, and a retro illumination refractometer.

In some embodiments, the apparatus further comprises a display device provided at an external surface of the housing, wherein the display device is configured to provide information messages to at least one of the subject and an observer within sight of the display device.

In some embodiments, the at least one optical measurement of the eye includes at least one of: a high order aberration of the eye, a pupil response characteristic, an external image of the eye, intraocular pressure of the eye, a fundoscope image of the eye, a corneal topography of the eye, an optical coherence tomography of the eye, and a blink rate of the eye.

In some embodiments, the apparatus further comprises a slit lamp illumination source for enabling a slit lamp examination of the eye.

In some embodiments, the apparatus further comprises a structured lighting device, wherein the structured lighting device is configured for at least one of: eye imaging, keratometry, eye motility testing, and slit lamp imaging of the eye.

In some embodiments, the structured lighting comprises a plurality of light-emitting diodes arranged in a pattern around the aperture.

In some embodiments, the structured lighting comprises a video display device.

In some embodiments, the structured lighting includes at least one Helmholtz-like back-lit aperture.

In some embodiments, the user interface includes at least a microphone for receiving voice communication from the subject, and a speaker for providing audio information to the subject.

In some embodiments, the user interface includes at least one camera capturing images of at least a portion of the eye, and an algorithm executed by the processing system for processing the captured images, for identifying at least one of eye blinks and gestures of the subject in the captured images, and for interpreting the at least one of the eye blinks, fixation gaze angle, facial and hand gestures as conscious feedback from the subject. Additional unconscious cues such as squinting, and pupil dilation may also be used advantageously in interacting with the patient.

In some embodiments, the user interface includes a camera for capturing images of the subject and a display device for displaying images to the subject.

In some embodiments, the apparatus further comprises: at least one light source configured to illuminate the eye; at least one camera configured to capture images of the eye; and a visual cue generator for presenting to the subject a visual cue for changing a gaze angle of the eye while capturing the images of the eye.

In some versions of these embodiments, the camera is configured to capture partial fundoscope images of a plurality of different portions of the eye at a corresponding plurality of different gaze angles, and the processing system is configured to stitch together the partial fundoscope images to produce a composite fundoscope image of the eye.

In some embodiments, the apparatus further comprises an air movement device which is configured to remove and dispose of airborne pathogens so as to prevent the airborne pathogens from contaminating the apparatus.

As also disclosed herein, an apparatus comprises: a processing system including a user interface; an eye measurement system including an optical system, wherein the eye measurement system is configured to make at least one optical measurement of an eye of a subject; a housing having the eye measurement system disposed therein, wherein the housing includes an aperture for providing light to and from the optical system and the eye while the subject is separated and spaced apart from the housing and while the eye is not maintained in a fixed positional relationship with respect to the housing; an optical system movement arrangement which is configured to move the optical system; an automatic eye tracking arrangement which is configured to ascertain a current positional relationship of the eye with respect to the optical system, and in response thereto to control the optical system movement arrangement to move the optical system into a predetermined positional relationship with respect to the eye; and a communication device, wherein the communication device is configured to communicate eye measurement data from the apparatus to an external remote terminal for evaluation. The eye measurement system includes: at least one objective refractive measurement device which is configured to make an objective refraction measurement of the eye via the optical system, a target, and a mirror system disposed in an optical path between the eye and the target for extending a length of the optical path, wherein the optical path further comprises at least one optical element of the optical system. The processing system is configured to interact with the subject via the user interface and in response to the interaction to adjust at least one parameter of the optical system to make a subjective refraction measurement of the eye based on the subject viewing the target. The communication device is further configured to receive instructions from the external remote terminal for adjusting at least one operating parameter of the apparatus.

As further disclosed herein, a method comprises: making at least one optical measurement of an eye of a subject with an eye measurement system including an optical system, wherein the eye measurement system is disposed within a housing, wherein the housing includes an aperture for providing light to and from the optical system and the eye while the subject is separated and spaced apart from the housing and while the eye is not maintained in a fixed positional relationship with respect to the housing; and ascertaining, via an automatic eye tracking arrangement without human assistance, a current positional relationship of the eye with respect to the optical system, and in response thereto moving the optical system into a predetermined positional relationship with respect to the eye without human assistance. Making the at least one optical measurement of the eye includes: making an objective refraction measurement of the eye via the optical system, and interacting with the subject via a user interface, and in response to the interaction adjusting at least one parameter of the optical system to make a subjective refraction measurement of the eye based on the subject viewing a target through an optical path which includes a mirror system between the eye and the target for extending a length of the optical path, wherein the optical path further comprises at least one optical element of the optical system.

As still further disclosed herein, a method comprises: making at least one optical measurement of an eye of a subject with an eye measurement system including an optical system, wherein the eye measurement system is disposed within a housing, wherein the housing includes an aperture for providing light to and from the optical system and the eye while the subject is separated and spaced apart from the housing and while the eye is not maintained in a fixed positional relationship with respect to the housing; and ascertaining, via an automatic eye tracking arrangement, a current positional relationship of the eye with respect to the optical system without necessary intervention from a human other than the subject, and in response thereto moving the optical system into a predetermined positional relationship with respect to the eye without necessary intervention from a human other than the subject. Making the at least one optical measurement of the eye includes: making an objective refraction measurement of the eye via the optical system, and interacting with the subject via a user interface and in response to the interaction adjusting at least one parameter of the optical system to make a subjective refraction measurement of the eye, without necessary intervention from a human other than the subject, based on the subject viewing a target through an optical path which includes a mirror system between the eye and the target for extending a length of the optical path, wherein the optical path further comprises at least one optical element of the optical system.

As yet further disclosed herein, a method, comprises: making at least one optical measurement of an eye of a subject with an eye measurement system including an optical system, wherein the eye measurement system is disposed within a housing, wherein the housing is disposed within an examination room, and wherein the housing includes an aperture for providing light to and from the optical system and the eye while the subject is separated and spaced apart from the housing and while the eye is not maintained in a fixed positional relationship with respect to the housing; and ascertaining, via an automatic eye tracking arrangement, a current positional relationship of the eye with respect to the optical system, and in response thereto moving the optical system into a predetermined positional relationship with respect to the eye without a presence of an ophthalmic technician in the examination room. Making the at least one optical measurement of the eye includes: making an objective refraction measurement of the eye via the optical system without the presence of the ophthalmic technician in the examination room, and interacting with the subject via a user interface and in response to the interaction adjusting at least one parameter of the optical system to make a subjective refraction measurement of the eye, without the presence of the ophthalmic technician in the examination room, based on the subject viewing a target through an optical path which includes a mirror system between the eye and the target for extending a length of the optical path, wherein the optical path further comprises at least one optical element of the optical system.

As even further disclosed herein, a method, comprises: making at least one optical measurement of an eye of a subject with an eye measurement system including an optical system, wherein the eye measurement system is disposed within a housing, wherein the housing includes an aperture for providing light to and from the optical system and the eye while the subject is separated and spaced apart from the housing and while the eye is not maintained in a fixed positional relationship with respect to the housing; and ascertaining, via an automatic eye tracking arrangement, a current positional relationship of the eye with respect to the optical system, and in response thereto moving the optical system into a predetermined positional relationship with respect to the eye. Making the at least one optical measurement of the eye includes: making an objective refraction measurement of the eye via the optical system, and interacting with the subject via a user interface and in response to the interaction adjusting at least one parameter of the optical system to make a subjective refraction measurement of the eye based on the subject viewing a target through an optical path which includes a mirror system between the eye and the target for extending a length of the optical path, wherein the optical path further comprises at least one optical element of the optical system. The method also includes: communicating eye measurement data from the apparatus to an external remote terminal for evaluation; and receiving instructions from the external remote terminal for adjusting at least one operating parameter of the eye measurement system.

As yet even further disclosed herein an apparatus comprises: a processing system including a user interface; an eye measurement system including an optical system, wherein the eye measurement system is configured to make at least one optical measurement of an eye of a subject; a housing having the eye measurement system disposed therein, wherein the housing includes an aperture for providing light to and from the optical system and the eye while the subject is separated and spaced apart from the housing and while the eye is not maintained in a fixed positional relationship with respect to the housing; an optical system movement arrangement which is configured to move the optical system; and an automatic eye tracking arrangement which is configured to ascertain a current positional relationship of the eye with respect to the optical system without a presence of an ophthalmic technician in the examination room, and in response thereto to control the optical system movement arrangement to move the optical system into a predetermined positional relationship with respect to the eye without a presence of an ophthalmic technician in the examination room. The eye measurement system includes: at least one objective refractive measurement device which is configured to make an objective refraction measurement of the eye via the optical system, a target, and a mirror system disposed in an optical path between the eye and the target for extending a length of the optical path, wherein the optical path further comprises at least one optical element of the optical system. The processing system is configured to interact with the subject via the user interface and in response to the interaction to adjust at least one parameter of the optical system to make a subjective refraction measurement of the eye based on the subject viewing the target.

As yet even further disclosed herein an apparatus comprises: a processing system having a user interface; an eye measurement system including an optical system, wherein the eye measurement system is configured to make at least one optical measurement of an eye of a subject; a housing having the eye measurement system disposed therein, wherein the housing includes an aperture for providing light to and from the optical system and the eye while the subject is separated and spaced apart from the housing and while the eye is not maintained in a fixed positional relationship with respect to the housing; an optical system movement arrangement which is configured to move the optical system; and an automatic eye tracking arrangement which is configured to ascertain a current positional relationship of the eye with respect to the optical system without necessary intervention from a human other than the subject, and in response thereto to control the optical system movement arrangement to move the optical system into a predetermined positional relationship with respect to the eye without necessary intervention from a human other than the subject. The eye measurement system includes: at least one objective refractive measurement device which is configured to make an objective refraction measurement of the eye via the optical system, a target, and a mirror system disposed in an optical path between the eye and the target for extending a length of the optical path, wherein the optical path further comprises at least one optical element of the optical system. The processing system is configured to interact with the subject via the user interface and in response to the interaction to adjust at least one parameter of the optical system to make a subjective refraction measurement of the eye based on the subject viewing the target.

BRIEF DESCRIPTION OF THE DRAWINGS

The example embodiments are best understood from the following detailed description when read with the accompanying drawing figures. Wherever applicable and practical, like reference numerals refer to like elements.

FIG. 19 illustrates an example of a web page which may be displayed on a subject's cell phone before, during and/or after an interaction with an eye examination apparatus.

DETAILED DESCRIPTION

In the following detailed description, for purposes of explanation and not limitation, example embodiments disclosing specific details are set forth in order to provide a thorough understanding of an embodiment according to the present teachings. However, it will be apparent to one having ordinary skill in the art having had the benefit of the present disclosure that other embodiments according to the present teachings that depart from the specific details disclosed herein remain within the scope of the appended claims. Moreover, descriptions of well-known apparati and methods may be omitted so as to not obscure the description of the example embodiments. Such methods and apparati are clearly within the scope of the present teachings.

Figure 1:
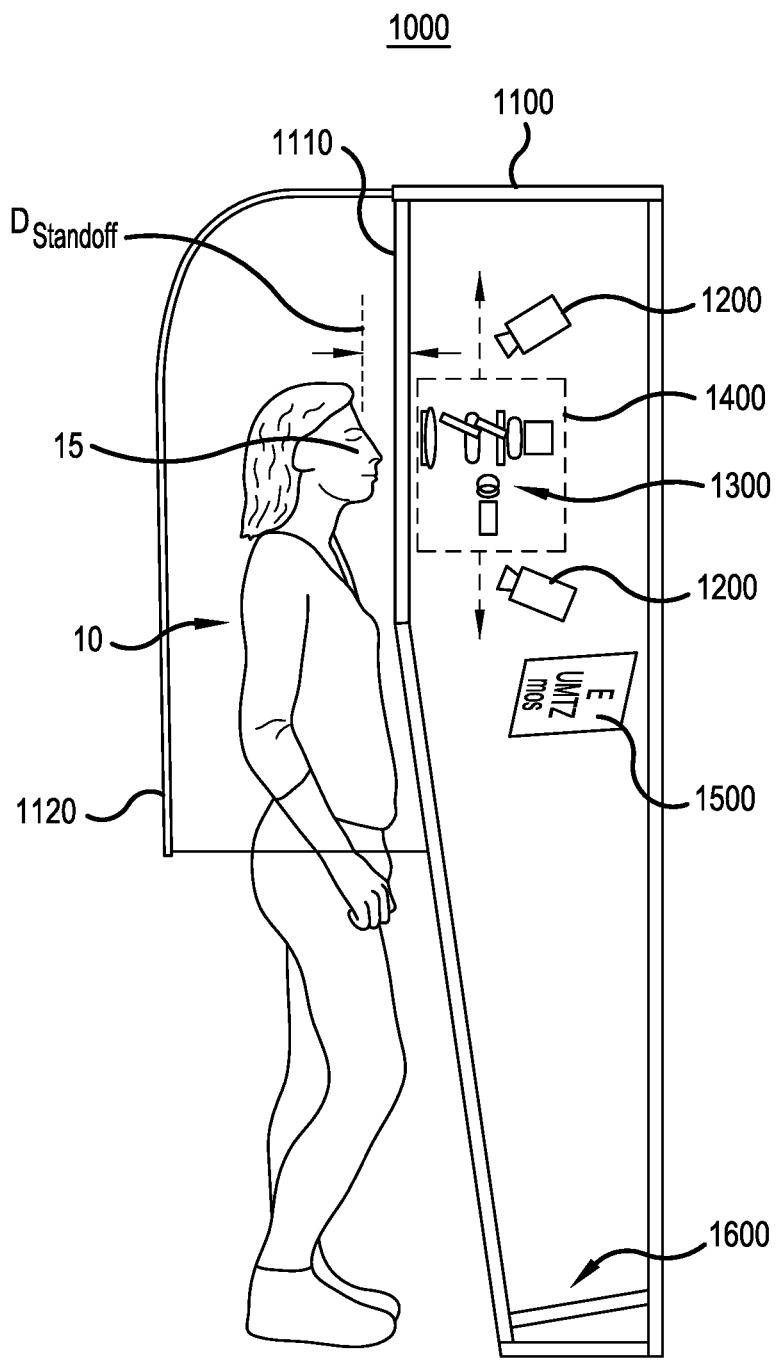
FIG. 1 illustrates a portion of an example embodiment of an automated non-contact eye examination apparatus for examining the eye of a subject.

FIG. 1 illustrates a portion of an example embodiment of an automated non-contact eye examination instrument or apparatus 1000 for performing an eye examination of one or both eyes 15 of a patient or subject 10. Apparatus 1000 includes a housing 1100. As described in greater detail below, housing has an aperture 1110 for providing light to and from one or more internal optical systems and one or both eyes 15 of subject 10 while subject 10 is separated and spaced apart from housing 1100 and while eye 15 is not maintained in a fixed positional relationship with respect to housing 1100. Here, an aperture may be defined as a space through which light passes between instrument or apparatus 1000 and one or both eyes 15 of subject 10. In some embodiments, aperture 1110 may comprise a hole or opening in housing 1100. In some embodiments, aperture 1110 may comprise a protective, light-transmissive or transparent, window through which light passes to and from one or more internal optical systems and one or both eyes 15 of subject 10.

Beneficially, the external surface of housing 1100 is smooth, allowing for quick and easy disinfection. Beneficially, the external surface of housing 1100 conforms to 3A sanitary standards.

In some embodiments, housing 1100 is provided with protective side shields 1120.

In some embodiments, an external surface of housing 1100 may be fabricated of, and/or coated with, an anti-microbial material.

Apparatus 1000 further includes: cameras 1200; at least one optical system 1300; an optical system movement arrangement 1400; an eye chart 1500 as a target for eye(s) 15 of subject 10; and a mirror system 1600 disposed in an optical path between eye 15 of subject 10 and the eye chart 1500. Mirror system 1600 lengthens an optical path between eye(s) 15 of subject 10 and eye chart 1500, effectively providing a viewing lane for subject 10 to view eye chart 1500, and accordingly may be referred to as a lane mirror arrangement. In some embodiments, apparatus 1000 may include two optical systems; one for each of the two eyes 15 of subject 10. In some embodiments, apparatus 1000 may include two optical system movement arrangements 1400; one for each optical system 1300 for each of a subject's two eyes 15. In other embodiments, apparatus 1000 may include one optical system movement arrangement 1400 which moves two optical systems 1300.

Figure 2:
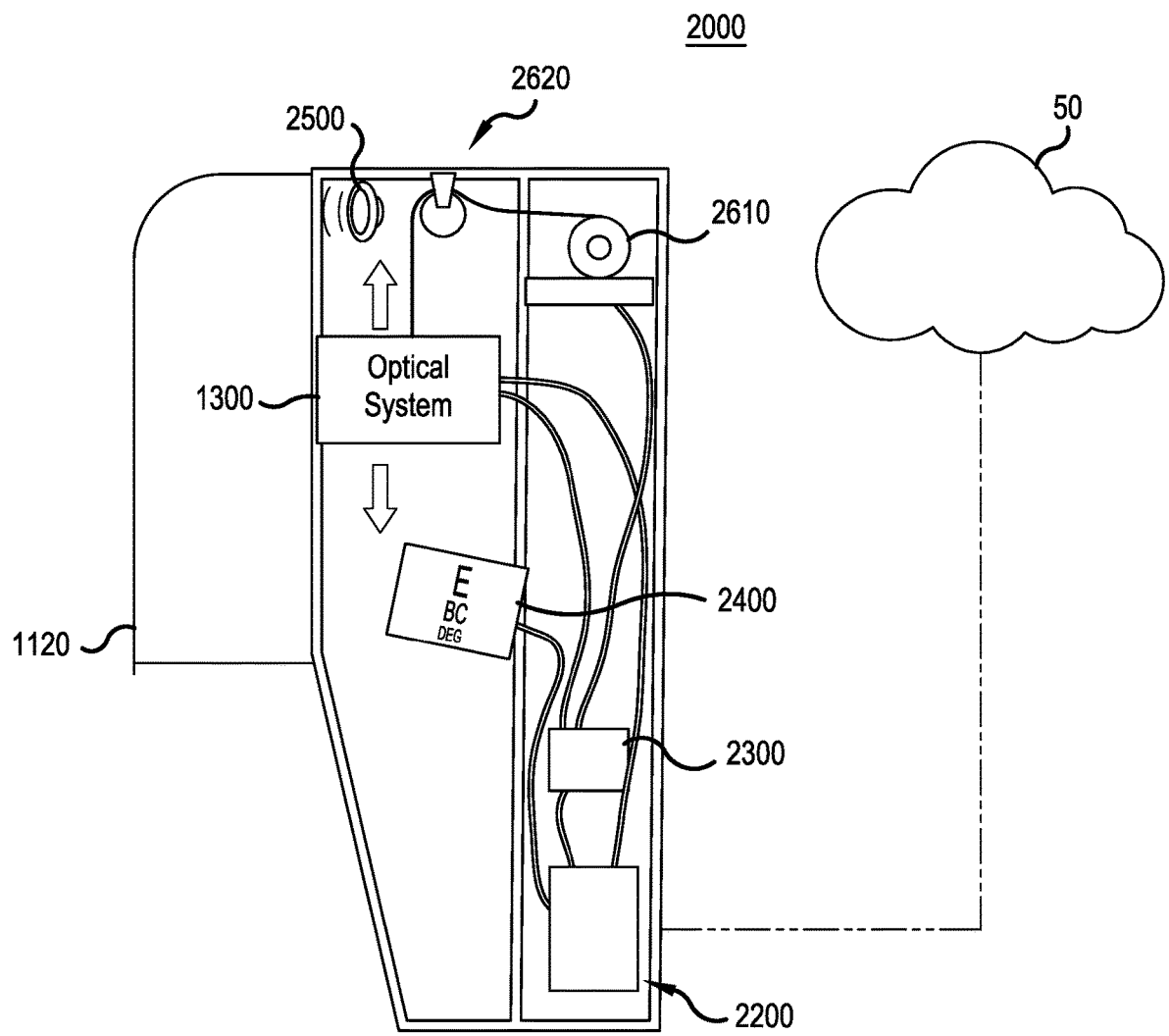
FIG. 2 illustrates another portion of an example embodiment of an automated non-contact eye examination apparatus.

FIG. 2 illustrates another portion of an example embodiment of an automated non-contact eye examination apparatus 2000. Eye examination apparatus 2000 may be one embodiment of eye examination apparatus 1000 of FIG. 1. FIG. 2 illustrates that eye examination apparatus 2000 includes optical system 1300, a processing system 2200, electronics 2300, a display device 2400, a speaker 2500, a motor 2610 and a pulley 2620. As with FIG. 1, automated non-contact eye examination apparatus 2000 may include two optical systems; one for each of the two eyes 15 of subject 10.

Processing system 2200 may include one or more processors and memory, including volatile and/or non-volatile memory. The memory may store therein instructions which may be executed by the one or more processors to execute any of the various algorithms or methods disclosed below.

Motor 2610 and pulley 2620 may comprises one embodiment of optical system movement arrangement 1400 of FIG. 1.

As shown in FIG. 2, eye examination apparatus 2000 may communicate to one or more external remote terminals via Internet 50. To that end, electronics 2300 may include a communication device (not shown) which may be wired and/or wireless and may communicate via WiFi, a wired Internet connection, a wireless mobile network (e.g., 4G or 5G), etc.

Some of the significant features of eye examination apparatus 1000 include the easily disinfected smooth outer shell or housing 1100 and the notable absence of the traditional headrest for subject 10. Eye measurement apparatus 1000 provides light to and from optical system 1300 and eye 15 of subject 10 while subject 10 is separated and spaced apart from housing 1100 and while eye 15 is not maintained in a fixed positional relationship with respect to housing 1100.

That is, in contrast to traditional ophthalmic instruments, eye examination apparatus 1000 does not require the head of subject 10 be constrained for eye measurements. Instead, eye examination apparatus 1000 includes an automatic eye tracking arrangement which is configured to ascertain a current positional relationship of eye 15 with respect to optical system 1300 (beneficially without human assistance), and in response thereto to control optical system movement arrangement 1400 to move optical system 1300 into a predetermined positional relationship with respect to eye 15 (again, beneficially without human assistance). The embodiment illustrated in FIG. 1 uses multiple cameras 1200 to automatically and continuously align the internal measurement modules (e.g., optical system 1300) of eye examination apparatus 1000 to eye(s) 15 of subject 10 during the measurements, regardless of normal subject motion. This concept eliminates the need for subject 10 to contact any surfaces of eye examination apparatus 1000, or to be in proximity to a technician during the measurements. Subject 10 does not even need to sit to have an eye examination.

Inside outer shell 1100, the use of spatial light modulators, a multi-function optical train, structured lighting, and head/eye tracking hardware may coordinate to provide subject 10 an experience that an eye examination is as simple as reading eye chart 1500. The optical paths for all measurements include a sufficiently large standoff, $D_{STANDOFF}$, to allow all measurements to take place with subject 10 standing comfortably distant from the protective window of aperture 1110. The eye measurement system may be capable of video rate captures of eye images and refraction measurements. Beneficially eye examination apparatus 1000 has a small footprint which allows multiple eye examination apparati 1000 to be co-located in the typically small examination rooms found in eye clinics.

Audio/visual cues may be provided to the patient by the eye examination apparatus 1000 and/or remotely by a technician or physician prior to, during, and/or after the eye examination. The added optional feature of a remote telemedical connection may allow eye examination apparatus 1000 to be conveniently located at places where it can be easily accessed by patients or subjects, by pre-arranged appointment, during the course of their normal workday activities.

In the United States, a complete eye examination requires the measurements and assessments shown in Table 1 below. Note that the Intraocular Pressure measurement is conducted to detect early-stage glaucoma, which may also be detected through fundoscopic examination.

mirrors may be mounted to housing 1100 so as to be stationary while LS5 is mounted to optical system 3500 that is free to move both vertically and horizontally as necessary to align itself to eye 15. The lane length is the optical distance between Image Plane 2 (shown in FIG. 4) and LS5. LS5 may be used to display traditional Snellen Eye Charts or similar targets upon which subject 10 may focus, as well as other icons or targets that may serve as fixation targets to manipulate the gaze angle of subject 10. This optical arrangement allows the lane length to remain constant as optical system 3500 is translated vertically. The lane length may be comparable to that used in traditional clinical lanes; e.g., 3 m or longer. The lane mirrors are sufficiently wide (out of diagram plane) to reflect light from LS5 onto Image Plane 2 (and thus eye 15) regardless of the horizontal position of optical system 3500. LS5 serves as the far refraction target traditionally used to measure the distance refraction correction of eye 15 during subjective refraction; it also acts as the fixation target during objective refraction measurement. Additionally, the lane mirrors and LS5 may serve both eyes 15 when eye examination apparatus 1000 is configured for binocular operation; such a configuration permits subject 10 to advantageously use convergence cues

TABLE 1

| Test/Function | Module | Reason/Diagnosis |
|---|---|---|
| Objective Refraction | Auto-refractor | Detect uncorrected refractive error |
| Subjective Refraction | Pre-Compensator | Refine refraction for prescription |
| Visual Acuity | Eye Display | Tests spatial frequency response of central visual field |
| Pupil Function | Eye Imager | Tests eye monocular and binocular eye response to light |
| Confrontation Visual Fields | Eye Imager | Tests peripheral visual system response to moving objects |
| Extraocular motility and alignment | Eye Imager | Tests stability of fixation and ability to smoothly track objects |
| External (anterior) Examination | Eye Imager | Detects pathologies of the eyelids and tissues surrounding the eye, e.g., trachoma |
| Slit Lamp Exam | Eye Imager | Detects pathologies in the anterior segment and cornea, e.g., corneal opacity, cataract |
| Fundoscopic Examination | Fundus Imager | Detects pathologies of the retina, e.g., age-related macular degeneration, diabetic retinopathy |
| Intraocular Pressure | Tonographer | Detects glaucoma |

In some embodiments, eye measurement apparatus 1000 is capable of performing all of the measurements and assessments listed in Table 1. In some embodiments, eye examination apparatus 1000 is capable of conducting remote refraction measurements without the presence of a technician, thus enabling corrective prescriptions for eyeglasses or contact lenses to be dispensed by a HCP immediately.

Figure 3:
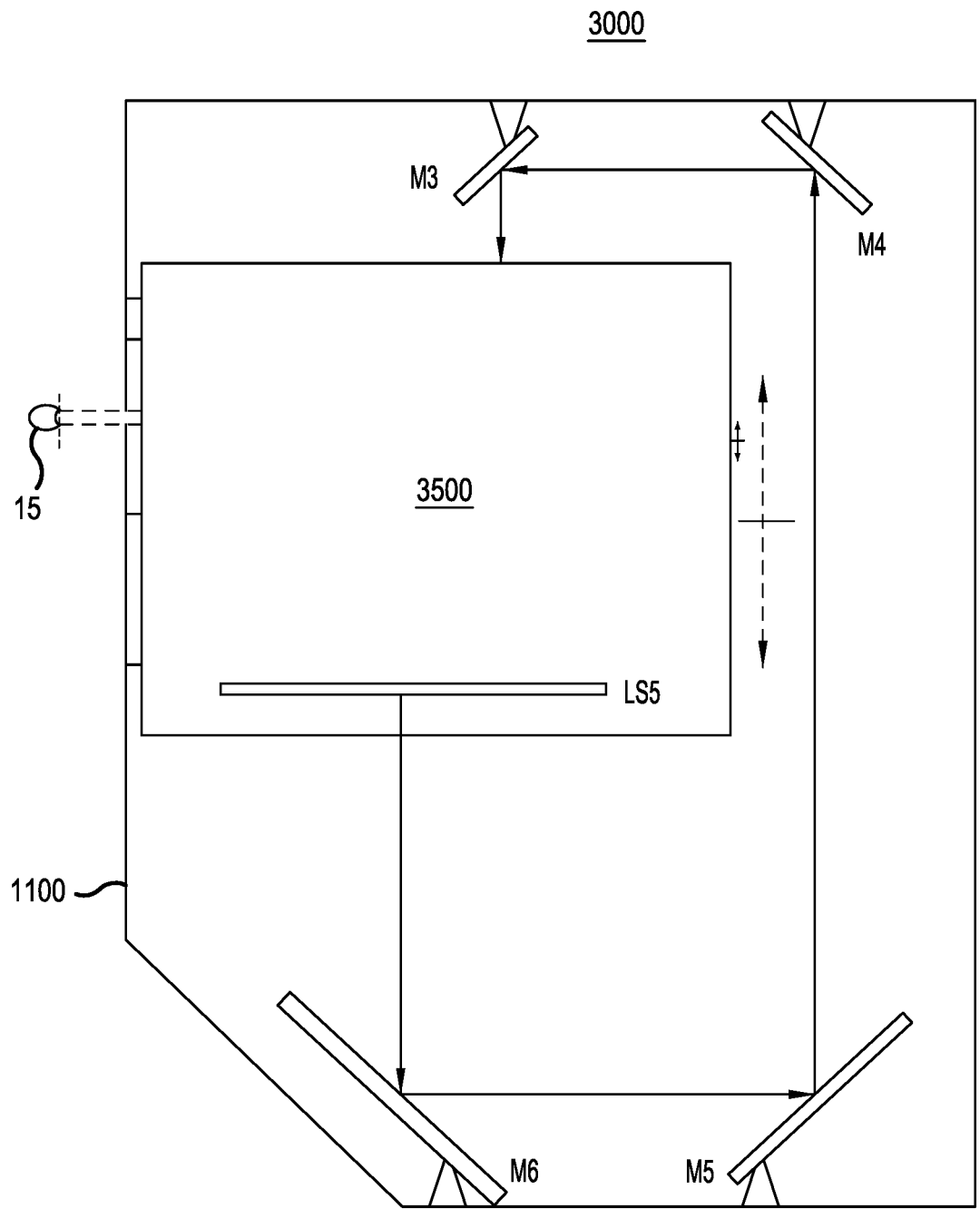
FIG. 3 illustrates an embodiment of an eye measurement system which may be included in an eye examination apparatus.

FIG. 3 illustrates an embodiment of an eye measurement system 3000 which may be included in an eye examination apparatus such as eye examination apparatus 1000.

Eye measurement system 3000 includes a lane mirror system and an optical system 3500, comprising optical devices and elements forming an optical path for eye measurement system 3000. Optical system 3000 is a specific embodiment of optical system 1300 of FIGS. 1 and 2.

Figure 4:
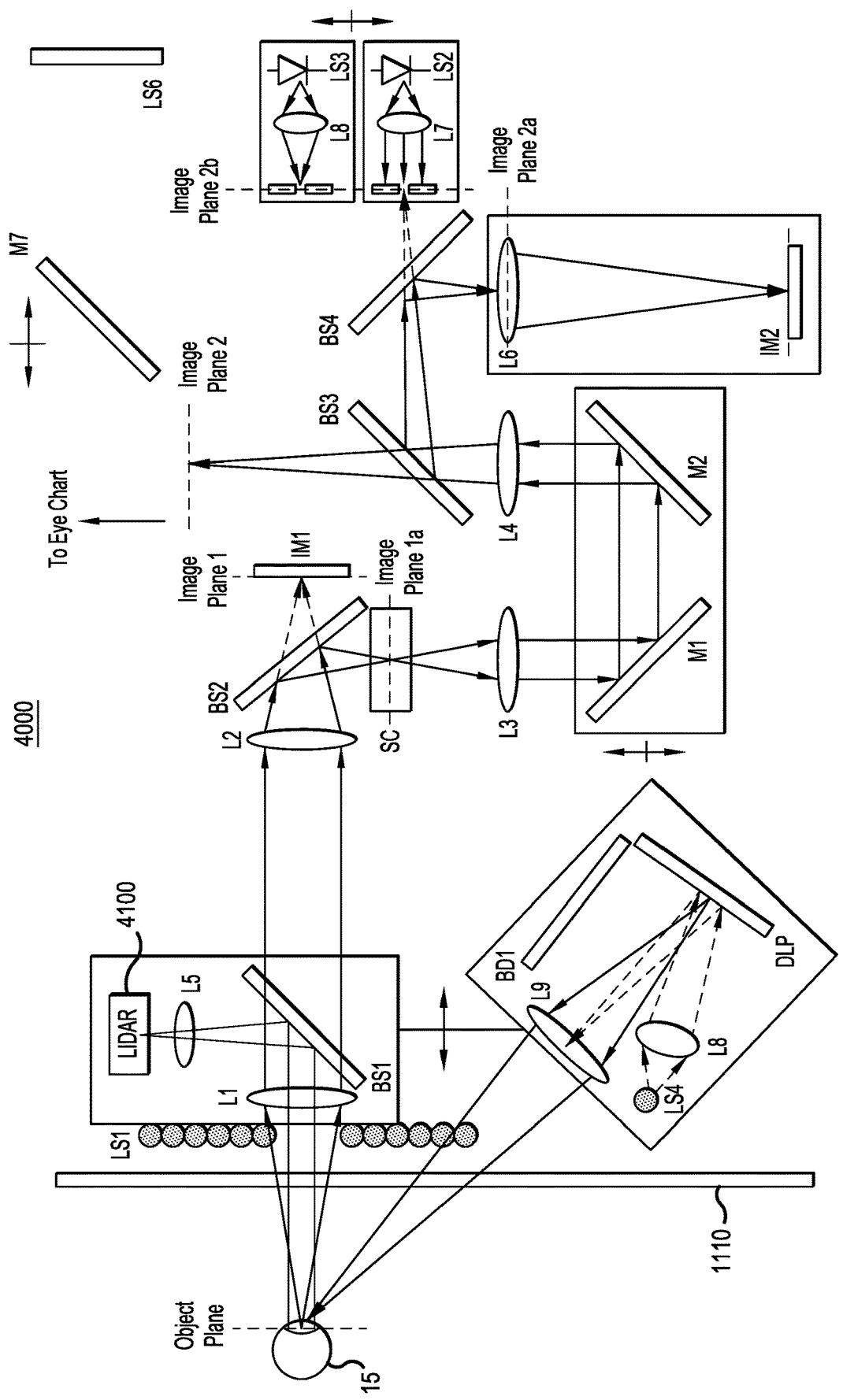
FIG. 4 illustrates an example embodiment of an optical system which may form part of an optical path for an eye measurement system.

FIG. 4 illustrates an example embodiment of an optical system 3000 comprising various light sources, sensors (or detectors), viewing targets, mirrors and other various optical elements forming an optical path for eye measurement system 3000. Optical system 3000 is a specific embodiment of optical system 3500 of FIG. 3, and will be described in greater detail below.

FIG. 3 shows the entire optical path including lane mirrors M3, M4, M5 and M6, eye chart display device LS5. All lane to perceive the target at full lane distance to reduce the likelihood of accommodation. An optional near target, LS6 (as shown in FIG. 4), may be mounted onto optical system 3500 at a distance 30-50 cm from Image Plane 2; by translating mirror M7 into the lane path, LS6 provides a near target for subjective and objective measurement of the near refraction correction for eyes 15 suffering from presbyopia.

Eye examination apparatus 1000 addresses two areas of critical importance that offer technical challenges: automated alignment and tracking of eye 15 required to achieve the needed optical alignment without contacting subject 10; and providing an optical configuration which has a sufficient optical standoff to permit robust isolation of eye examination apparatus 1000 and subject 10.

Regarding the former, in the past eye alignment has typically required the head of subject 10 to be constrained while the eye measurement system is brought to the desired object plane and the x and y positions (e.g., pupil center). The object plane of the optical system is typically designed to be fixed focus relative to the body of the apparatus. Alignment is achieved by monitoring the x and y positions of a desired fiducial while the z position is adjusted to bring the image into focus. Once alignment is achieved, one or a few measurement images may be captured (e.g., Shack-Hartmann wavefront images).

In contrast, for embodiments of the automated eye examination apparatus 1000, subject 10 is not required to be constrained and is subject to motion in 6 dimensions: three positions and three angles. However, rather than design the automated alignment and tracking system to apply alignment corrections of eye examination apparatus 1000 in all dimensions, in some embodiments, variance is accommodated in the z dimension through proper optical design. In this case, optical system 4000 may be already constrained to the distal side of the protective window of aperture 1110. This may be accomplished through a variable focus component. In some embodiments, alignment cameras 1200 are capable of detecting and measuring z distance, cyclo-rotation, and gaze angle variations which can be used to compensate the measurements or to filter images from the video stream that exceed the desired tolerances. Note that the interpupillary distance must also be considered in this binocular instrument, however, this distance only need be adjusted at the start of the measurement sequence. With these choices, an automatic eye alignment and tracking system simplifies to correcting only lateral (x) and vertical corrections (y) while measuring the remaining 4 dimensions. The angle ranges measured are further bounded by providing a visual target for eye 15 to look at while being measured. Deviations may occur from saccadic movements which can be detected and excluded when necessary.

In optical system 4000, eye tracking may be accomplished through the inclusion of a Light Detection and Ranging ("LIDAR") device 4100 as described in greater detail below with respect to FIG. 11.

Figure 5:
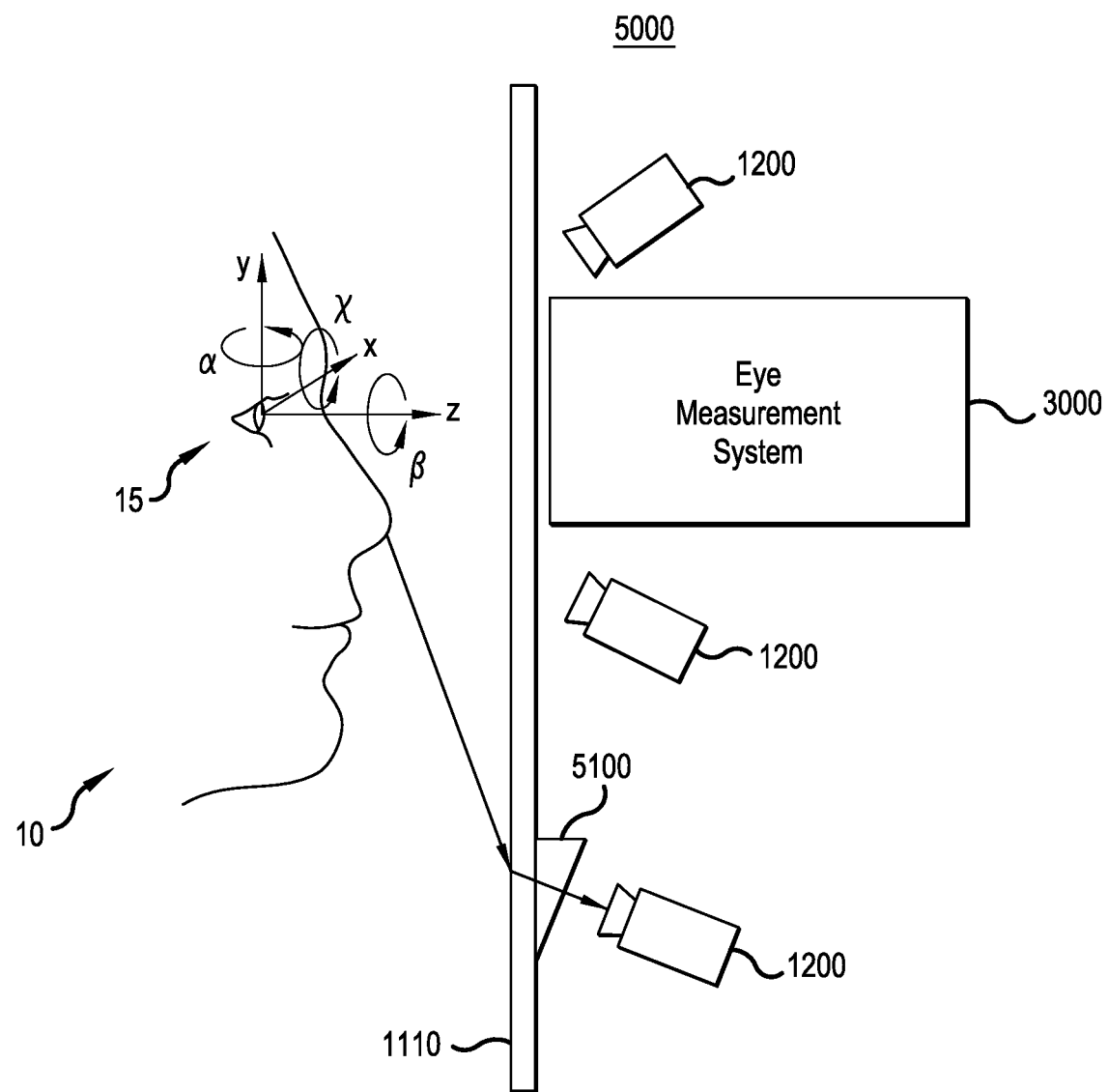
FIG. 5 illustrates an example embodiment of an eye alignment arrangement.

FIG. 5 illustrates another example embodiment of an eye alignment arrangement which incorporates cameras 1200. This optical system uses two or more imaging cameras 1200 to provide 6-dimensional (e.g., $x,y,z,\alpha,\beta,\chi$) position and rotation information of the position of subject 10 relative eye examination apparatus 1000 to permit accurate, real-time alignment of optical system 3500 to subject 10. Structured or unstructured lighting may optionally be supplied to improve the accuracy of the alignment. The two primary features to be tracked include the eye pupils. Cameras 1200 may be stationary with respect to eye examination apparatus 1000, or may move with or independent of optical system 3500. Cameras may optionally be equipped with prisms 5100 to increase the oblique angles that can be captured.

Regarding the optical configuration, eye measurement system may include a variable phoropter/autorefractor, and an eye imaging arrangement including an imaging device (e.g., a camera) for imaging anterior and posterior segments of eye 15.

Figure 6:
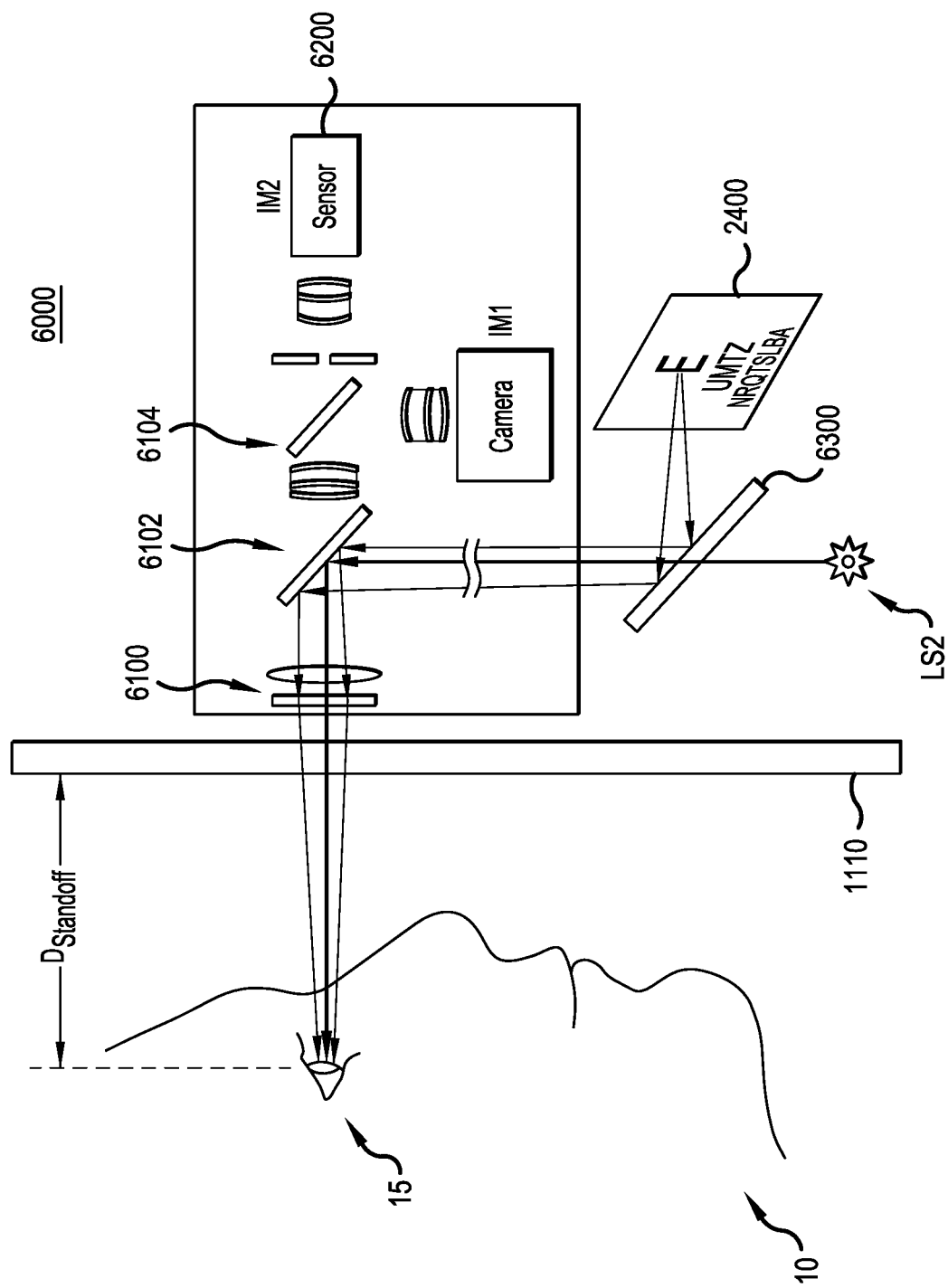
FIG. 6 illustrates elements of an example embodiment of an autorefractor.

Manifest refraction is the gold standard for measuring refraction of eye 15. FIG. 6 below illustrates an embodiment of eye examination apparatus which includes as a pre-compensation section 6100 a phoropter which comprises lenses that can be inserted into the line of sight of eye 15 while subject 10 views a distant object (e.g., Snellen eye chart at 4 meters distance). The physician may systematically vary the sphere value and the cylinder magnitude and axis while asking subject 10 to compare between lens combinations as to which is clearer. Such subjective refraction generally may be first done monocularly, but ultimately verified binocularly. To ensure that subject 10 has relaxed accommodation, additional plus lenses are often added to ensure the target becomes noticeably less focused. The lenses in the phoropter come in 0.25 Diopter increments, limiting the accuracy of measurement to what is typically achieved in eyeglasses and contact lenses. The repeatability of the measurement is limited to a standard deviation of 0.319 D by the subjective feedback and is highly dependent on the skill of the physician, particularly with respect to correcting the magnitude and axis of the cylinder component.

FIG. 6 illustrates elements of an example embodiment of an autorefractor 6000. Autorefractor 6000 includes, among other things, light source LS2, pre-compensation section 6100, beam splitters 6102 and 6104, a wavefront sensor 6200, and lane mirror 6300.

In some embodiments, an autorefractor uses a Badal optometer as pre-compensation section 6100 through which subject 10 views an optical fixation target. The target is conveniently projected into eye 15 with a vergence at optical infinity or beyond (fogging) to stimulate subject 10 into relaxing accommodation as when viewing an actual object at a large distance. Light source LS2, having passed through the pre-compensation section and the anterior of the eye focuses onto the patient's retina and scatters backwards toward autorefractor 6000. Sensor 6200 (e.g., a Shack-Hartmann wavefront detector, a phase diversity sensor, a pyramid sensor, a curvature sensor, a point spread function (PSF) sensor, a retro illumination refractometer, etc.) monitors the wavefront emanating from "guide star light" injected into eye 15 and scattering from the retina that passes through pre-compensation section 6100, as discussed below with respect to FIGS. 7-11. Calibrated pre-compensating section 6100, such as a Badal optometer, in the sensing branch serves to subtract sphere and cylinder from the wavefront impinging on sensor 6200 such that it remains within its measurement range. The total wavefront from eye 15 is the sum of the pre-compensation values and the residual wavefront measured on sensor 6200. With each successive measurement of the wavefront, the pre-compensation section 6100 may be adjusted to further reduce the wavefront curvature. This iterative process continues until the measured wavefront curvature it is within the desired tolerance; the process may then terminate and the final refraction reported. Measurement precision approaching 0.1 D is routinely obtained with properly designed autorefractors.

While the auto refractor affords better precision than manifest refraction, traditional autorefractors seldom achieve the same level of accuracy as manifest refraction. The unnatural target projected at large optical distance does not effectively relax accommodation because other visual cues of distance are missing. In particular, the autorefractor is most often a monocular device that excludes convergence cues to distance; other cues can also make the subject perceive the target closer (e.g., looking into a small instrument or a small tube). These factors frequently lead to "instrument accommodation" that can amount to a large fraction of a diopter of error. The cylinder magnitude and axis, on the other hand, are very accurately measured by an autorefractor.

In contrast to existing instruments, eye examination apparatus 1000 may support (simultaneous) manifest refraction and autorefraction measurements using the same optical system 1300, and both can be combined to yield higher accuracy results. In some embodiments, autorefractor 6000 incorporates corrective lenses positioned at a variable optical standoff of 150-200 mm and a real, dynamically programmable target (on an electronic display) at a distance presented to the subject in binocular format. The distant real target mitigates "instrument accommodation" by subject 10. While similar to the manifest refraction set up, this innovative approach raises challenges because the refractive correction is placed far from the normal spectacle plane (about 12.5 mm from eye vertex) where phoropter lenses would be placed and may introduce unwanted, unnatural optical distortions (e.g., tilt). Fortunately, the mathematics of ray tracing is well established, and these distortions can be modelled and corrected. The corrective power of this pre-compensation section can be remotely adjusted in response to feedback from subject 10. The refractive measurement from the autorefractor may be advantageously used to initially adjust the pre-compensation section prior to manifest refraction. With the final correction in place, the HCP can conduct traditional subjective visual acuity testing much as they would with a phoropter, except that the lens adjustment for this scenario is electronically controlled. In this way the advantages of the accuracy of a phoropter and manifest refraction can be combined with the precision of the autorefractor. Indeed, eye examination apparatus 1000 may deliver both subjective refraction (manifest refraction) and objective refraction (autorefraction) measurements.

Figure 7:
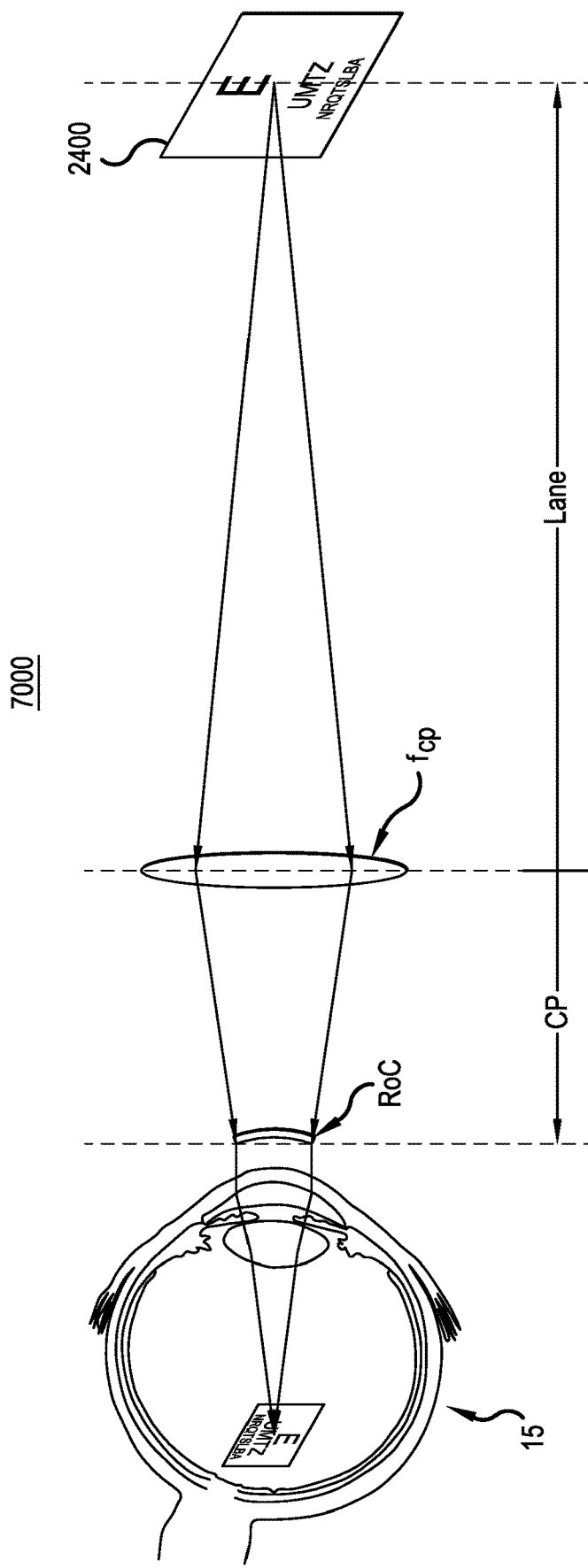
FIG. 7 illustrates some principles of a pre-compensation section of an eye measurement system.

FIG. 7 illustrates some principles of a pre-compensation section of an eye measurement system.

The effective focal length, fcp, when located at the correction plane, at distance CP from eye 15, for a target at distance Lane, will bring the target into best focus on the retina of the dis-accommodated eye 15.

Equation 1 below shows how the RoC, the radius of curvature of the wavefront at the corneal vertex, is related to fcp, CP, and Lane; RoC is positive for hyperopes, negative for myopes, and infinity for a true emmetrope.

$$\frac{1}{f_{cp}} = \frac{1}{RoC + CP} + \frac{1}{\text{Lane}} = Rx_{cp} \qquad \text{Equation 1}$$

The measurement of RoC can be done at any convenient distance CP.

Lane is typically >3 meters in most eye clinics.

Given the RoC for each subject eye 15, the physician prescribes refractive corrections, $Rx_{cp}$, using Equation 1 with CP=0 for contact lenses and refractive surgeries, and to about 0.0125 meters for eyeglasses.

The purpose of the pre-compensation section is to compensate the subject's refractive error (sphero-cylindrical) so the subject sees the target clearly. The effective focal length, $f_{cp}$, of the pre-compensation section is adjusted to bring the target into focus when eye 16 is dis-accommodated. Dis-accommodation may be accomplished by manually fogging (as in manifest refraction) or with an interactive algorithm (as in autorefractors). When eye 15 is dis-accommodated and the sphero-cylindrical correction of the pre-compensation section has been adjusted to produce best focus of the target for the subject, the radius of curvature (RoC) of the wavefront meridians just outside the cornea can be determined mathematically. The measured RoCs can then be used to prescribe the appropriate sphero-cylindrical refractive correction (e.g., contact lenses, eyeglasses, or refractive surgery) for subject 10.

Various embodiments of pre-compensation may be accomplished with a variety of techniques. In its simplest embodiment, the pre-compensation section may comprise a collection of lenses much like in a phoropter. Other embodiments include the incorporation of variable power pre-compensation elements such as variable focal length lenses (e.g., liquid lenses), a wide angle Badal optometer that employs moving optics on linear stages, variable mirrors (e.g., adaptive optics deformable mirror), a phase only spatial light modulator, or a retroreflection refractor, or combinations of the above.

In one such embodiment, a phase only spatial light modulator (SLM) may be coupled with helper lenses to the same effect but with higher speed and with the ability to pre-compensate cylinder at any axis. The SLM is capable of providing variable spherocylindrical correction over some dynamic range (e.g., ±5 D), which can be added to the helper lens(es) to span the relevant refractive correction range of human eyes (−16 to +8 D sphere, and 0 to −6 D cylinder). Like the variable power options which act to reduce the number of corrective lenses and mechanical complexity while improving the resolution of measurement below 0.25 diopters, the SLM introduces the ability to also correct for unwanted distortions such as tip/tilt as the subject moves laterally. These variable power options also can compensate for subject motion that introduces variations in the optical standoff which would otherwise affect the measurement.

SLMs generally only supply about a $2\pi$ of phase delay but can do so at spatial resolutions approaching 4160(h)×2464 (v) using 3.45 μm pixels at refresh rates approaching 60 Hz. With this density, it is possible to create a variable power Fresnel lens with sphero-cylinder power up to ±5 diopters over a 6 mm diameter aperture. Furthermore, the center of this correction can be rapidly shifted to compensate for lateral eye movement. The high refresh rate permits the apparent compensation of chromatic aberration normally attributed to diffractive lenses when used with polychromatic targets. Color field sequential display rapidly sequentially displays the primary colors in the target while the subject views through corresponding corrected diffractive patterns; color fusion is accomplished in the human visual system.

The final power of the pre-compensating element can be mathematically converted into a prescription for eyeglasses, contact lenses or refractive surgery using simple paraxial ray tracing formulas like Equation 1.

Returning to FIG. 4, FIG. 4 shows the schematic diagram of the optical path of eye measurement system 3000. Eye 15 is shown at the far left.

Light from light sources LS1, LS2, LS3, or LS4 may illuminate eye 15 and create reflected and scattered light that travels toward eye measurement system 3000 entering through aperture or window W1. L1 captures this light and fully or partially collimates it for analysis. Light travels through BS1 which may preferentially reflect wavelengths longer than 900 nm and/or may be designed to preferentially reflect S polarized light; BS2 may transmit shorter wavelengths. As discussed in greater detail below with respect to FIGS. 8-11, optical system 4000 includes a relay imager comprising lenses L1 and L2 and a Badal optometer comprising lenses L3 and L4 as a pre-compensation section which is configurable to bring the target into focus on eye 15 for making the subjective refraction measurement of the subject's eye 15.

LIDAR device 4100 may be fixed to lens L1; L1 may move to bring the relay imager into focus. L2 is the second lens of the relay imager and this focusses the light from eye 15 onto a two-dimensional imaging sensor or camera IM1, positioned at Image Plane 1. BS2 is a partial reflector that allows light from eye 15 to reach IM1 to complete the eye imaging section of optical system 4000.

The light reflected by BS2 travels through a Stokes Cell ("SC"), which allows for continuously adjustable astigmatic correction; SC is positioned at Image Plane 1a which is equidistant from BS2 as Image Plane 1. Spherical correction is accomplished with the Badal optometer comprised of lenses L3 and L4 and mirrors M1 and M2. Mirrors M1 and M3 can be translated simultaneously to change the distance between L3 and L4, thereby providing continuously adjustable spherical correction. BS3 is also a partial reflector for visible light and a high reflector for near infrared (NIR) light. The transmitted visible light allows subject 10 to view the eye chart; Image Plane 2 represents the optical position of eye 15, with refractive correction applied, when viewing the targets LS5 or LS6. The remaining visible and NIR light may be directed toward a wavefront or similar sensor; a point spread function (PSF) sensor is shown in FIG. 4. Light is focused by lens L6, positioned at Image Plane 2a (equidistant from BS3 as Image Plane 2) onto imaging sensor IM2; the size and shape of the formed spot can be analyzed to advantageously to drive the Stokes Cell and Badal optometer to correct for eye refractive errors.

Imaging sensor IM2 measures the radius of curvature of the wavefront of light from eye 15 using well-known 'guide-star' techniques. Imaging sensor IM2 may include any of the following: a Shack-Hartmann Sensor, a Phase Diversity Sensor, a Pyramid Sensor, a Curvature Sensor, a point spread function (PSF) Sensor, or a Retro-illumination refractometer. Additional lenses may be included as required to bring the scattered wavefront onto the imaging sensor IM2 for proper measurement.

Light source LS2 may be a NIR super luminescent diode or LED that provides a narrow beam light (e.g., 2 mm diameter) collimated by lens L7 and can be used to create a tight spot on the retina of eye 15 to act as a "guide star." The output aperture for LS2 is positioned at Image Plane 2a to ensure that the light is imaged onto the Object Plane. LS3 is an alternate light source which may be divergent in contrast to that produced by LS2; it may be used to flood illuminate the retina when imaging the fundus. Like LS2, its output aperture may be approximately 2 mm and is positioned at Image Plane 2a. LS2 and LS3 may be physically translated into position or optically or electronically switched.

FIGS. 8a, 8b and 8c illustrate an example embodiment of a pre-compensation section 8000 of an eye measurement system, including a relay imager 8100 and a Badal optometer 8200.

Figure 8:
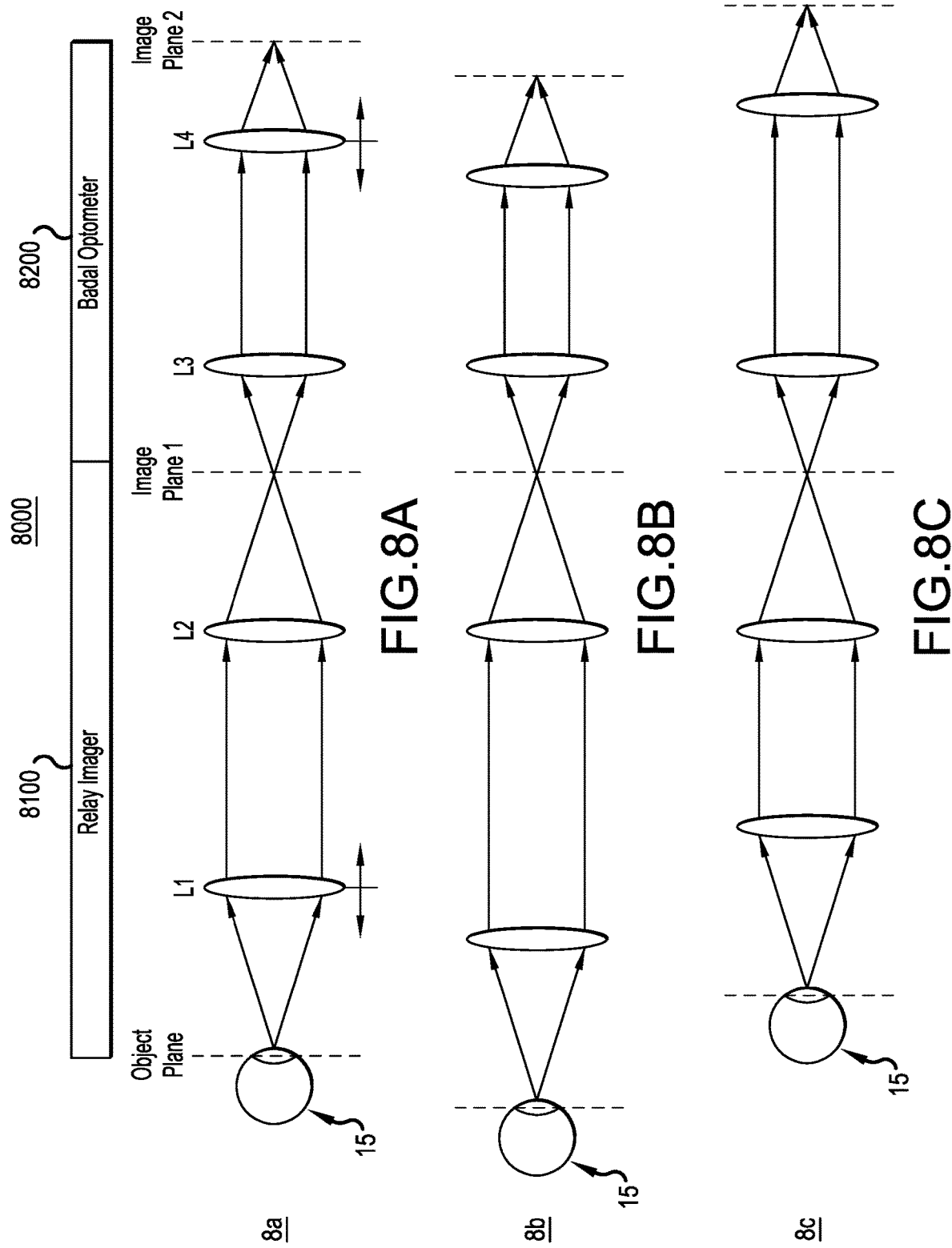
FIG. 8a, FIG. 8b and FIG. 8c illustrate an example embodiment of a pre-compensation section of an eye measurement system.

This configuration has the advantage of providing a sharp eye image to monitor eye alignment and the current eye state (e.g., open or closed eyelids) while measuring and providing a target with proper refractive correction to the subject. The target is not shown in FIG. 8 but would be to the right of the position labelled Image Plane 2. FIG. 8a illustrates the nominal lens positions for a nominal position of eye 15 relative to the optical system. FIG. 8b illustrates the lens positions when eye 15 is positioned further from the optical system than in FIG. 8a. FIG. 8c illustrates the lens positions when eye 15 is positioned closer to the optical system than in FIG. 8a. Note that the positions of lenses L2 and L3 do not change.

In this embodiment, Relay Imager 8100 casts a sharp image of eye 15 at Image Plane 1 while Badal Optometer 8200 relays that image onto Image Plane 2 while also adjusting the wavefront curvature to as to compensate for the refractive error of eye 15. Relay Imager 8100 consists of two lenses, L1 and L2 of focal length f1 and f2, respectively. Relay Imager 8100 will have its object plane a distance f1 from L1 and its image plane at a distance f2 from L2. This produces an image with fixed magnification −f2/f1 at Image Plane 1. The motion of eye 15 is tracked by translating lens L1 to maintain a distance of f1 to eye 15, thus ensuring that a sharp image of eye 15 will always appear at Image Plane 1 independent of the position of eye 15 relative to the optical system. The distance between L1 and eye 15 may be maintained by actuating the position of L1 according to an autofocus algorithm or by direct measurement the distance by using a LIDAR device or other distance sensor.

Badal Optometer 8200 similarly consists of two lenses, L3 and L4 with focal lengths f3 and f4. A continuous range of refractive correction may be applied to the wavefront curvature by adjusting the distance between L3 and L4. By advantageously placing an astigmatic correction device (e.g., a Stokes cell) at Image Plane 1, Badal optometer 8200 can correct for both spherical and cylindrical refractive errors.

Relay Imager 8100 has the drawback that it may alter the wavefront curvature at Image Planes 1 and 2 depending on the separation between L1 and L2. However, this correction is deterministic and can be compensated through a small adjustment of the distance between L3 and L4 as shown in FIGS. 9 and 10.

Figure 9:
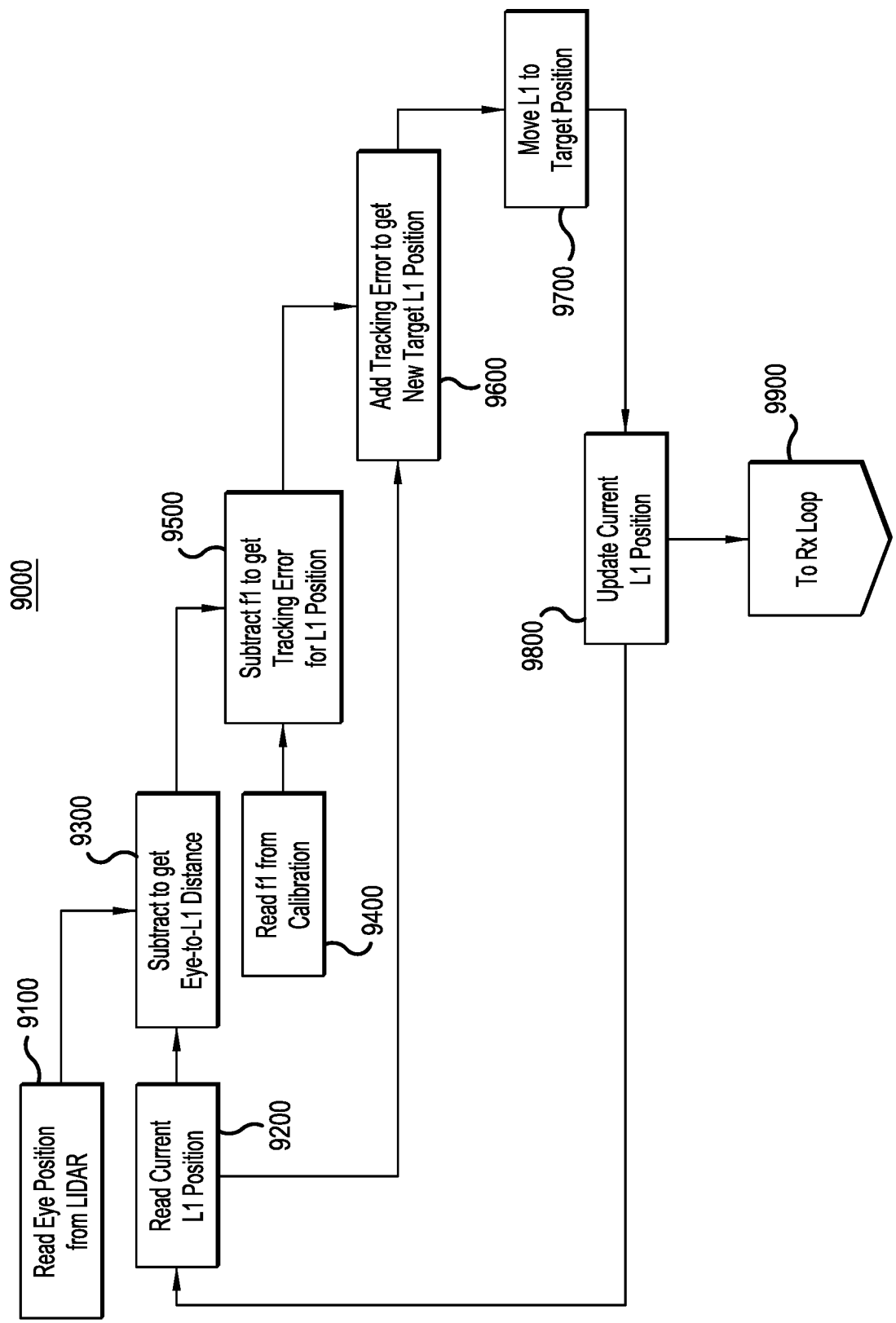
FIG. 9 illustrates an example embodiment of an operation of a focus loop of the pre-compensation section of FIG. 8.
Figure 10:
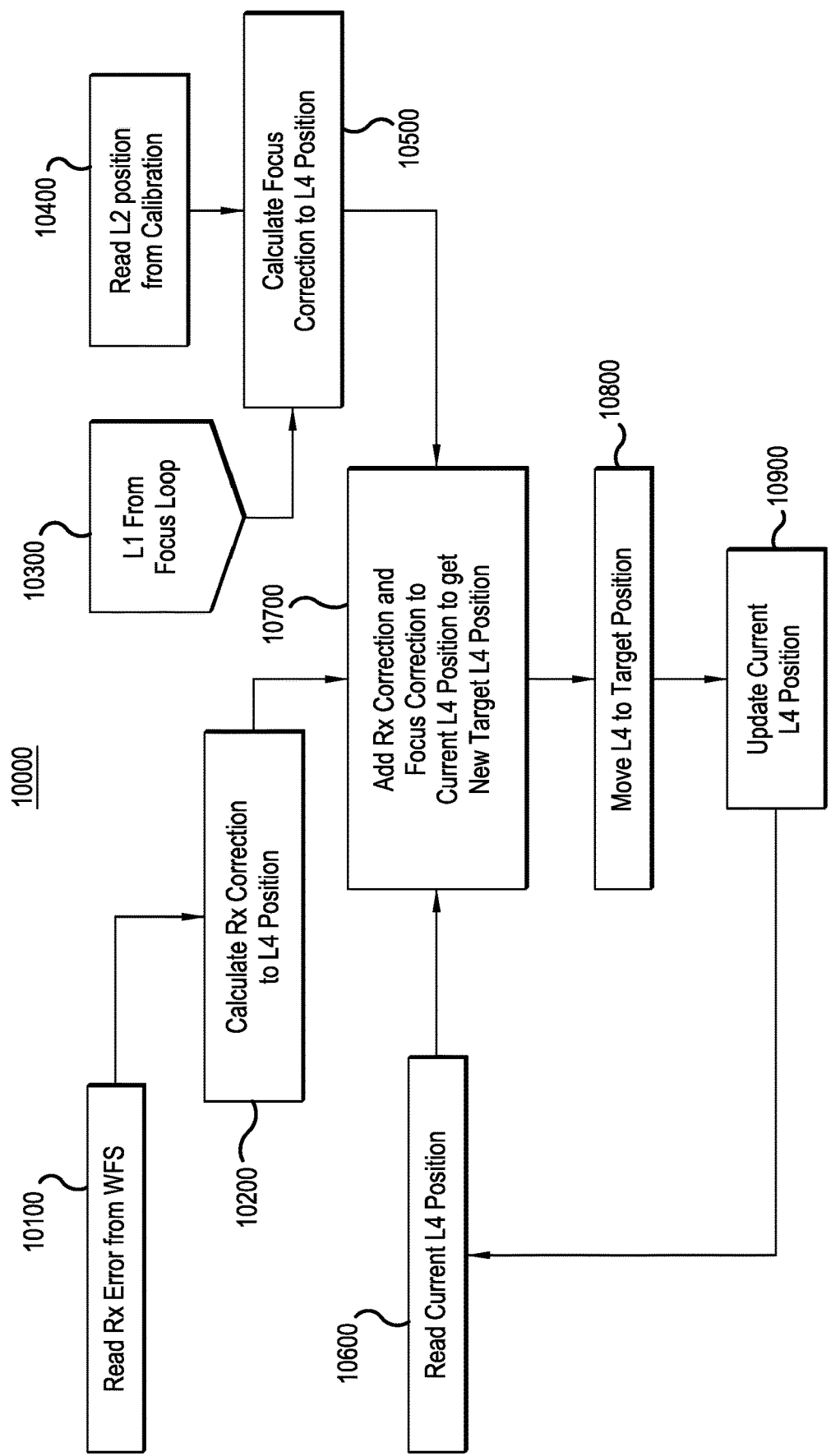
FIG. 10 illustrates an example embodiment of an operation of a refraction correction loop of the pre-compensation section of FIG. 8.

FIG. 9 illustrates an example embodiment of an operation of a focus loop 9000 of the pre-compensation section of FIG. 8. Focus loop 9000 may be implemented by software stored in memory and which is executed by a processor, such as by processing system 2200.

Operation 9100 includes reading the position of eye 15 from LIDAR device 4100.

Operation 9200 includes reading the current position of lens L1.

Operation 9300 includes subtracting the positions obtains in operations 9100 and 9200 to obtain the eye-to-L1 distance.

Operation 9400 includes reading f1 (focal length of lens L1) from calibration data.

Operation 9500 includes subtracting f1 from the eye-to-L1 distance to obtain the tracking error for the position of lens L1.

Operation 9600 includes adding the tracking error to the current position of lens L1 to obtain a new target position for lens L1.

Operation 9700 includes moving lens L1 to the new target position.

Operation 9800 includes updating the current position of lens L1.

Operation 9900 includes providing the updated current position of lens L1 to the refraction correction loop of FIG. 10.

FIG. 10 illustrates an example embodiment of an operation of a refraction correction loop 10000 of the pre-compensation section of FIG. 8. Refraction correction loop 10000 may be implemented by software stored in memory and which is executed by a processor, such as by processing system 2200.

Operation 10100 includes reading the refraction error from a wavefront sensor.

Operation 10200 includes calculating the refractive correction to the position of lens L4.

Operation 10300 includes obtaining the position of lens L1 from the focus loop 9000.

Operation 10400 includes reading the position of lens L2 from calibration data.

Operation 10500 includes calculating a focus correction to the position of lens L4 from the outputs of operations 10300 and 10400.

Operation 10600 includes reading the current position of lens L4.

Operation 10700 includes adding the refraction correction and the focus correction to the current position of lens L4 to obtain a new target position for lens L4.

Operation 10800 includes moving the lens L4 to the target position.

Operation 10900 includes updating the current position of lens L4.

Figure 11:
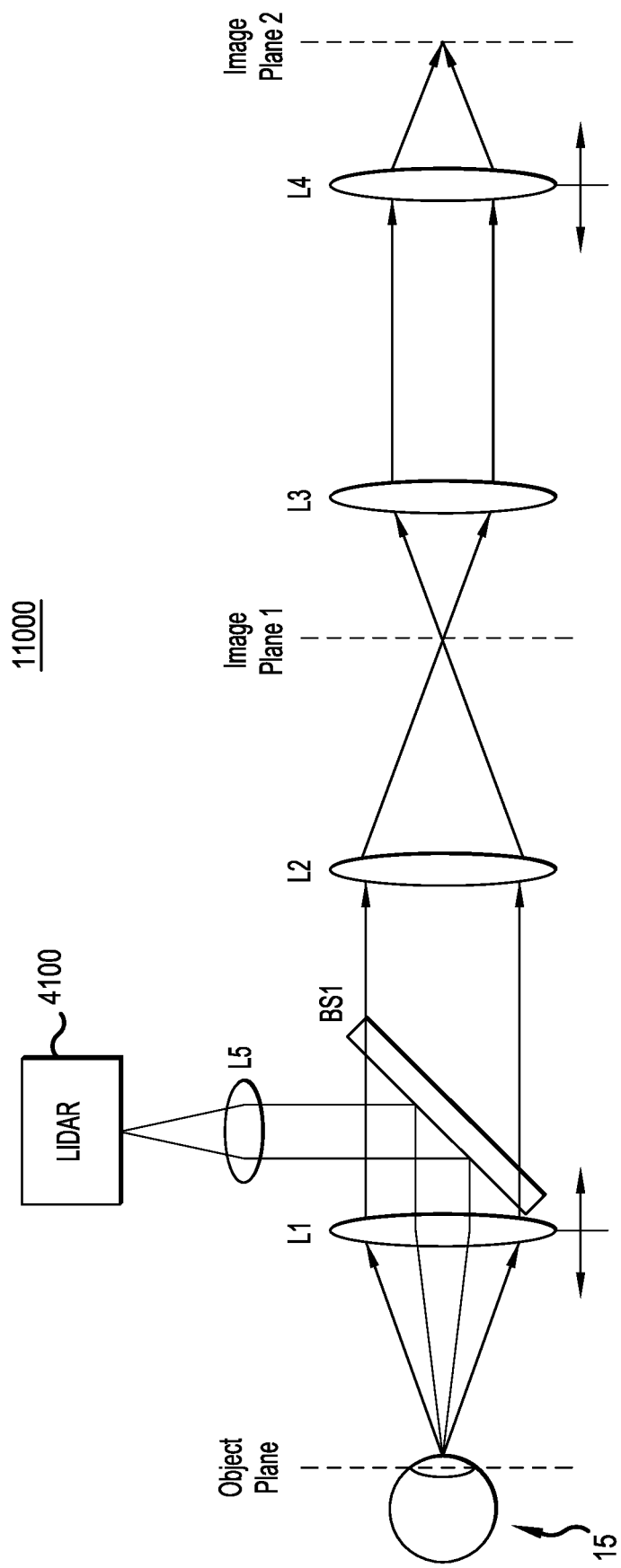
FIG. 11 illustrates an example embodiment of a pre-compensation section of an eye measurement system which is provided with a Light Detection and Ranging ("LIDAR") device.

FIG. 11 illustrates an example embodiment of a pre-compensation section 11000 of an eye measurement system which is provided with LIDAR device 4100.

The use of LIDAR device 4100 simplifies the control algorithm compared to an autofocus algorithm by reducing the calculations required in each control iteration. Compact LIDAR devices 4100 are commercially available with a range and distance accuracy compatible with such an embodiment. In this case, LIDAR device 4100 can be mounted to move with L1 to directly measure distance from L1 to eye 15. LIDAR device 4100 may also be advantageously optically positioned at Image Plane 1 or 2 to employ the optical system to ensure that only light reflected from the cornea is used in the ranging. FIG. 11 illustrates how the light from LIDAR device 4100 may be collimated with lens L5 and sent through L1 to focus on the cornea. In this case, lens L5, beam splitter BS1, and the LIDAR unit may move with L1.

Figure 12:
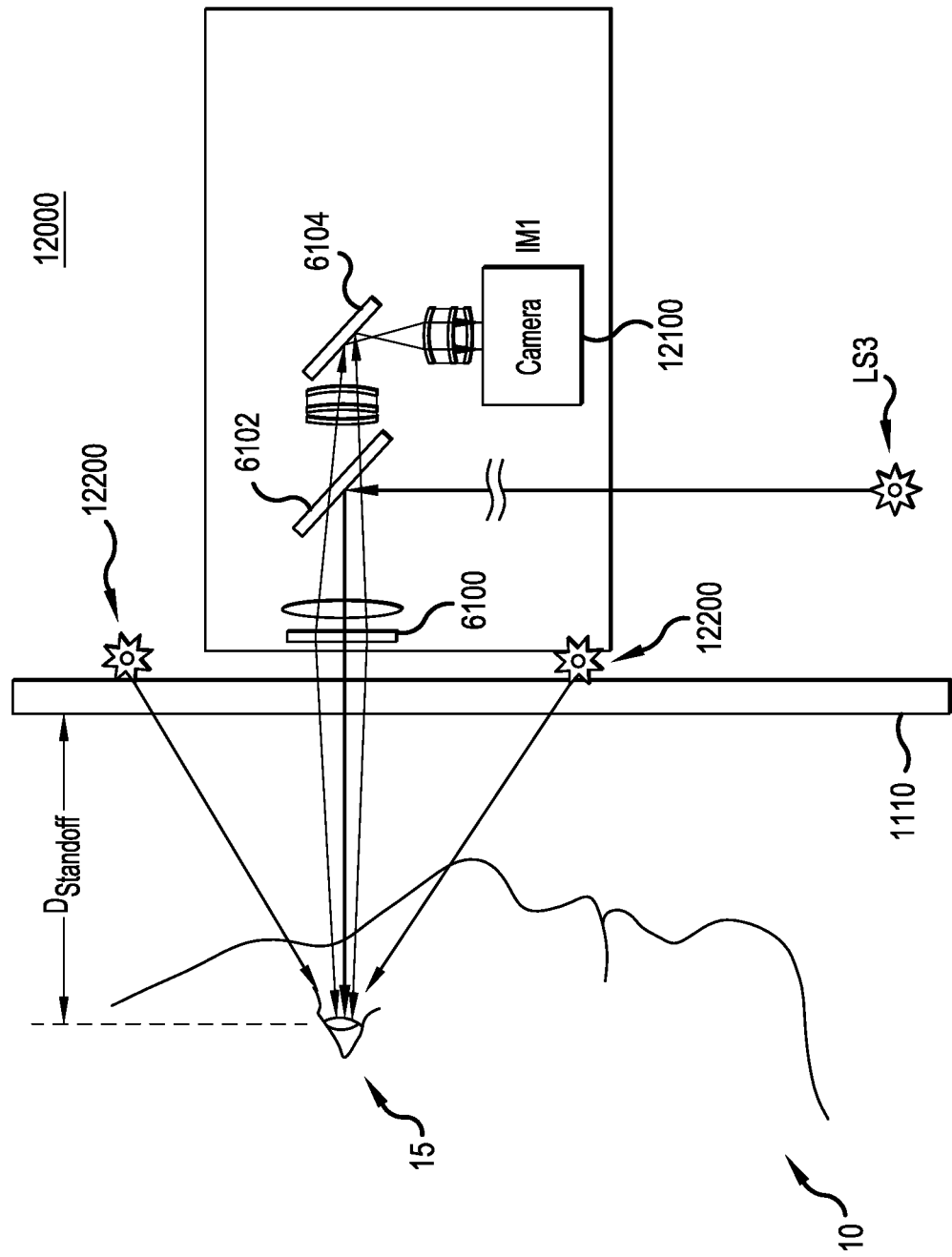
FIG. 12 illustrates an external eye examination system using light sources to provide illumination of the eye.

FIG. 12 illustrates an external eye examination system 12000 using light sources to provide illumination of eye 15, for example for capturing images of eye 15 using camera 12100.

Images of the exterior of eye 15 are useful for testing pupil function, external examination for pathologies of eye 15 and surrounding tissues, to test extraocular motility and alignment. Imaging of the anterior of eye 15 with appropriate lighting from lighting elements 12200 may permit some level of slit lamp examination. Finally, imaging of the posterior of eye 15 allows examination of the fundus. In some embodiments, each of these imaging systems could be independently designed and simply mounted at a different location in the eye alignment and tracking system Two or more cameras 12100 may supply video images of both eyes 15 to test pupil response, ocular motility, visual confrontation, and for external and internal examination of eyes 15 and nearby structures (e.g., eyelids).

Different visual stimuli may be applied through peripheral or coaxial light sources for each examination element.

Light sources 12200 may be fixed relative to the field of view or may move within it; some light sources may be structured (e.g., images of fingers, or a narrow bright slit); some may be arranged in an array, as described below with respect to FIG. 13.

In some embodiments, pre-compensation section 6100 of the optical system may be adjusted to obtain magnified images of the internal or external area of eye 15.

In some embodiments, pre-compensation section 6100 may be used to produce an aerial image that is subsequently conditioned to match camera 12100. The image can stay in focus despite changes in standoff distance; small magnification differences so introduced can be compensated in the display of the image and in the quantitative analyses as well. The use of additional light sources 12200 can not only illuminate eye 15 and surrounding tissue, but also can be used for keratometry and corneal topography if desired. Light sources 12200 can also provide stimuli to the subject for pupil and confrontation visual field and extraocular motility and alignment testing. In some cases, lighting 12200 may be controlled to smoothly translate across areas of the peripheral field of view of subject 10. In a much similar way, slit lamp examination can be simulated with this same arrangement.

Figure 13:
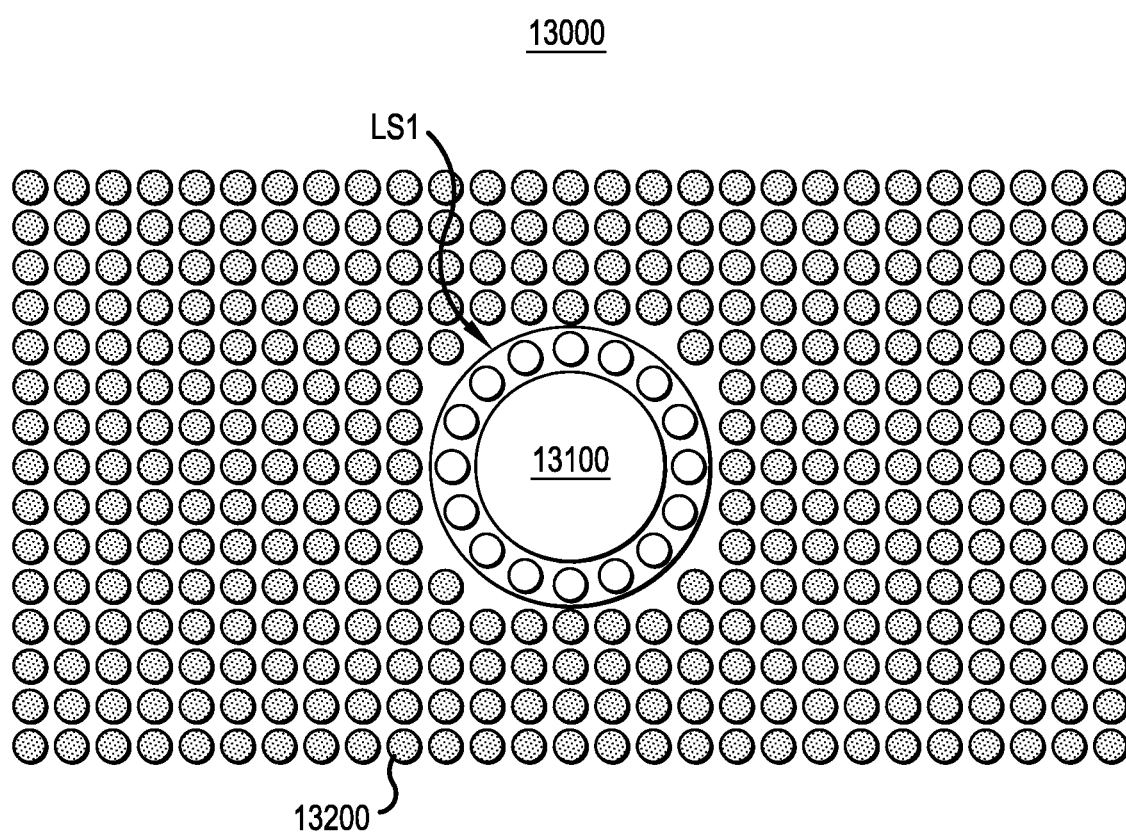
FIG. 13 illustrates an example embodiment of a structured lighting arrangement which may be used to illuminate the eye and to create new fixation directions to facilitate ocular measurements.

FIG. 13 illustrates an example embodiment of a structured lighting arrangement 13000 which may be used to illuminate eye 15 and to create new fixation directions to facilitate ocular measurements.

Structured lighting may be used to illuminate eye 15 and to create new fixation directions to facilitate ocular measurements. Each dot in FIG. 13 represents an individually addressable light source 13200. The ring pattern around aperture 13100 may be symmetrically disposed around the optic axis of the optical system and may be used to illuminate eye 15 for eye imaging and/or for keratometric measurement. The array of peripheral light sources 13200 may be used for corneal topographic measurements and/or to test the integrity of the tear film surface when activated in concert, and/or can act as fixation points to change the gaze of subject 10 for slit lamp examination, for extraocular motility, and confrontation visual field testing.

Figure 14:
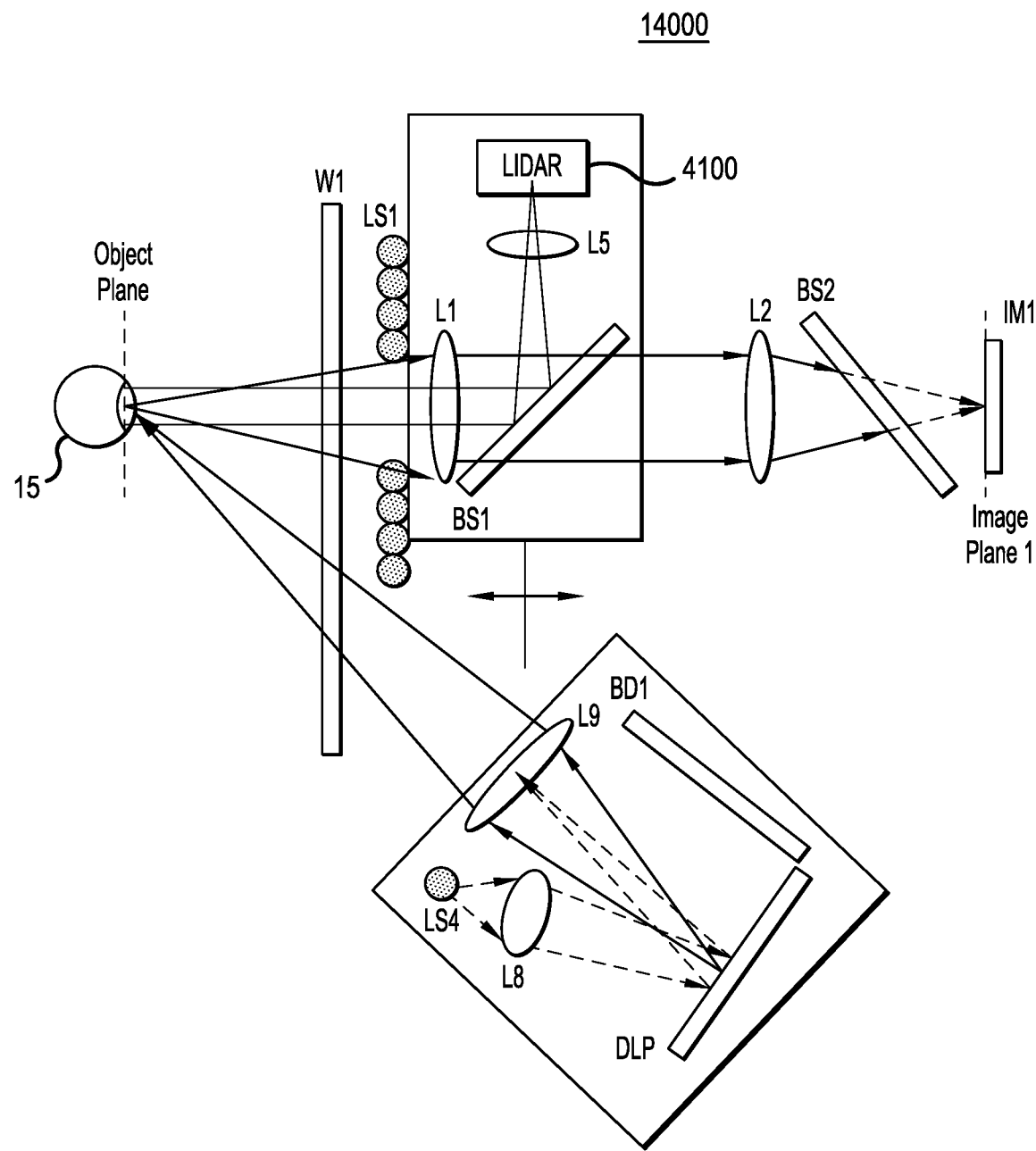
FIG. 14 illustrates an example embodiment of a slit lamp illuminator of an eye measurement system.
Figure 15:
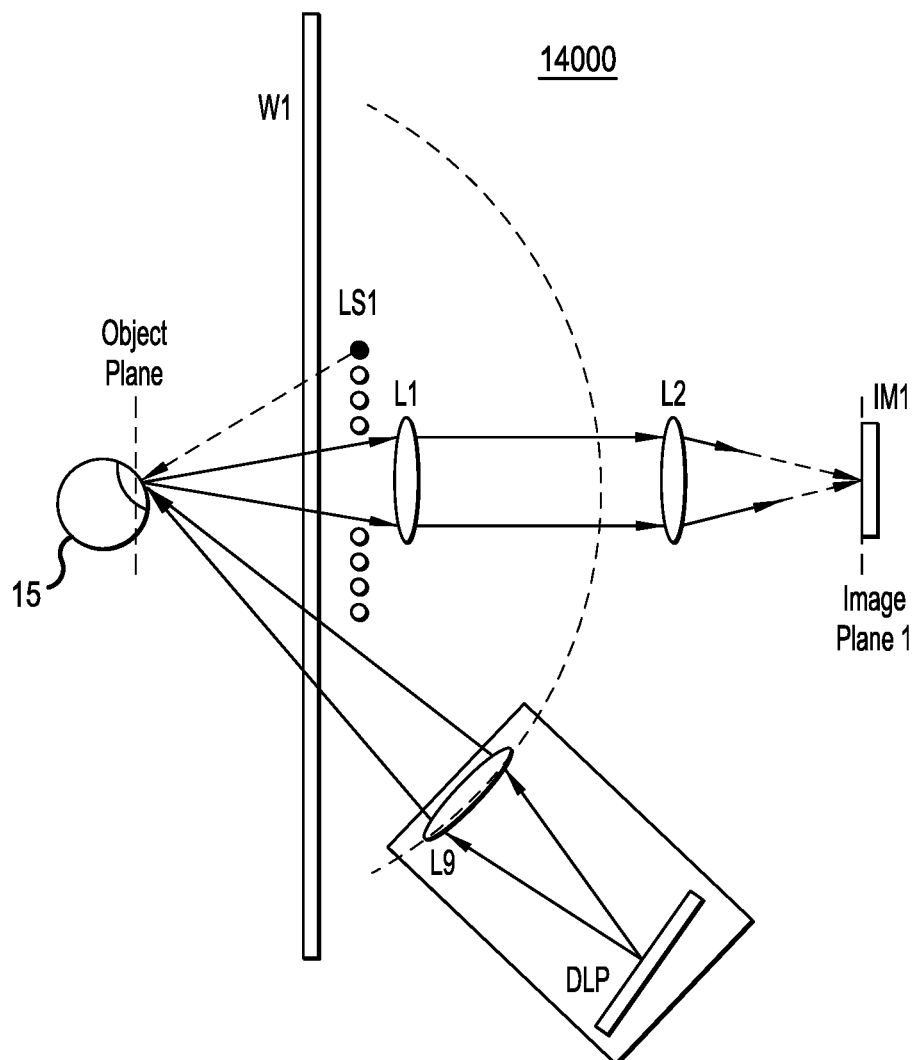
FIG. 15 shows a bottom view of the slit lamp illuminator of FIG. 14.

FIG. 14 illustrates an example embodiment of a slit lamp illuminator 14000 of an eye measurement system. The slit lamp illumination is from below eye 15 and utilizes a Kholer configuration. Light source LS4 is imaged onto projector lens L9 by condenser lens L8. The slit is created electronically on digital light processing chip, DLP, to form arbitrarily shaped apertures whose dimensions can be controlled electronically with approximately 10 μm resolution and which can be changed at video rates in synchrony with image captures on for example by processing system 2200. The slit illuminator assembly also comprises a beam dump, BD1, which may absorb all unwanted light from LS4. This assembly is suspended above or below the LIDAR assembly and moves with the optic assembly 3500 to maintain alignment with the eye as it moves. The slit lamp illuminator assembly may also rotate about a vertical axis located at eye 15, as shown in FIG. 15, to allow an operator (e.g., a HCP controlling slit lamp illuminator from an external remote terminal via a communication device of eye examination apparatus 1000) to change the angle of incidence continuously over a range of ±60° from the optic axis. Fine positioning of the light image on eye 15 can be accomplished electronically with the DLP. The observation angle for the scattered light can be adjusted by using a selected LED on LS1 to create a fixation target upon which the subject can fixate, thereby rotating eye 15 and thus the observation angle.

FIG. 15 shows a bottom view of the slit lamp illuminator of FIG. 14.

Figure 16:
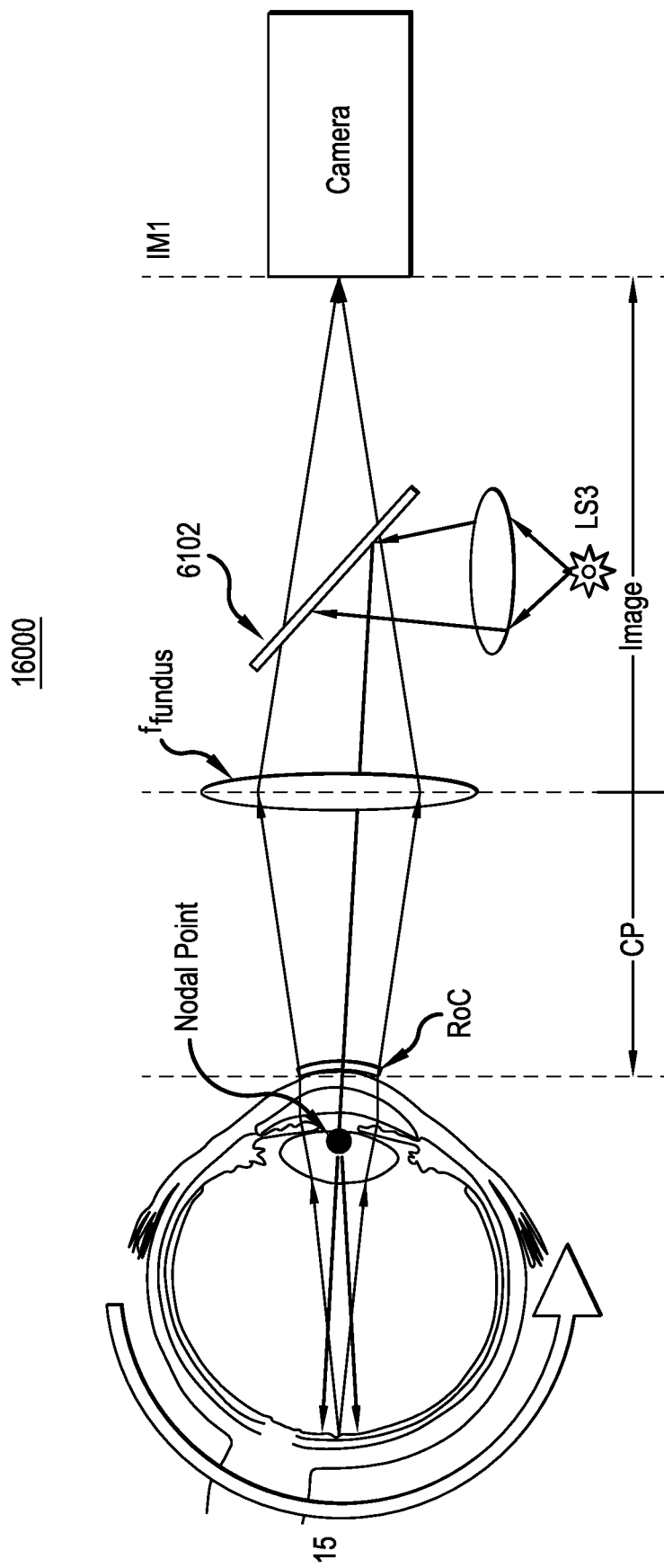
FIG. 16 illustrates how an example embodiment of an eye measurement system may obtain a fundus image of an eye.

FIG. 16 illustrates how an example embodiment of an eye measurement system may obtain a fundus image of an eye.

Equation 2 below may be applied with respect to FIG. 16:

$$\frac{1}{f_{fundus}} = \frac{1}{RoC + CP} + \frac{1}{\text{Image}} \qquad \text{Equation 2}$$

In some embodiments, a fundus imager may invoke different gaze angles for subject 10 using structured lighting 13200 to attain multiple images with a small field of view which can be stitched together into a high field of view image of the fundus.

Fundus imaging also may benefit from the pre-compensation section of the optical system, discussed above. In this case lighting is directed into eye 15 and knowledge of the refractive state of eye 15 may simplify maintaining focus.

The case shown in FIG. 16 is essentially direct ophthalmoscopy where the lighting is directed through the nodal point of eye 15 to illuminate a large section of the fundus. To obtain high angle coverage of the fundus, subject 10 may be stimulated to gaze in different directions with lighting that creates a moving target while images are captured continuously. Processing system 2200 may employ image processing to undistort the images and then use fundus landmarks to stitch them into a large field of view fundus image.

Figure 17:
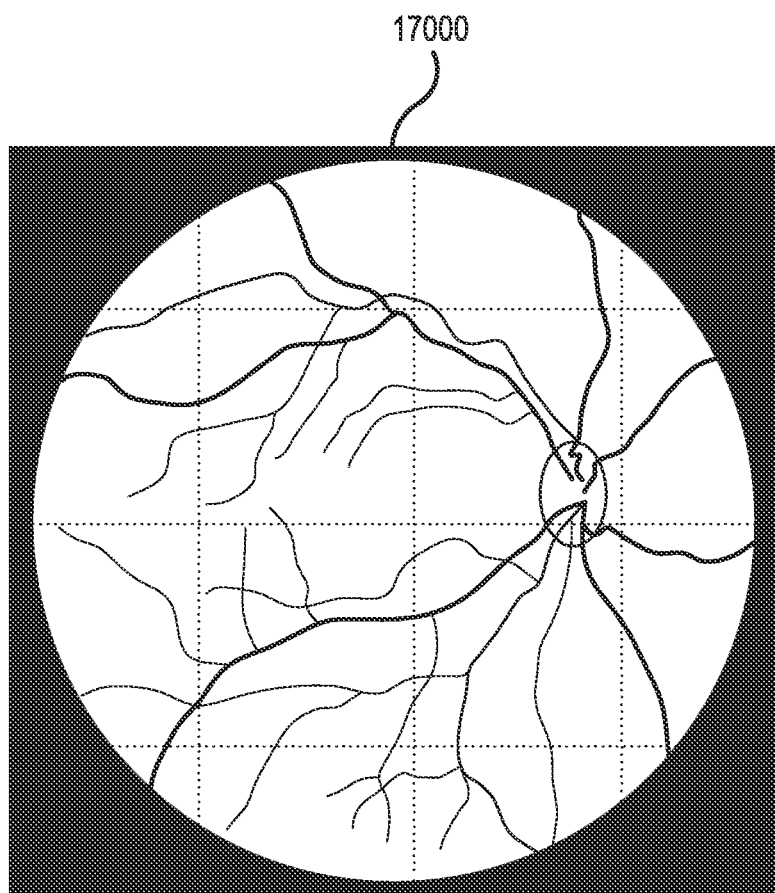
FIG. 17 illustrates an example of a fundus image of an eye.

FIG. 17 illustrates an example of a fundus image 17000 of eye 15 which may be obtained by eye examination apparatus 1000 and eye measurement system 3000 as discussed above with respect to FIG. 16.

In some embodiments, eye examination apparatus 1000 may include a tonographer (not shown), and in that case the presence and progression of glaucoma may be derived from tonographer measurements. In other embodiments, fundoscopy of eye 15 allows the eye examination apparatus 1000 to test for glaucoma of eye 15. Examples of a technique for glaucoma detection from a fundus image are disclosed in Shilpa Sameer Kanse, et al., "Retinal Fundus Image for Glaucoma Detection—A Review and Study," J. INTELL. SYST. 2017, the entirety of which is hereby incorporated by reference herein as if fully set forth herein.

Figure 18:
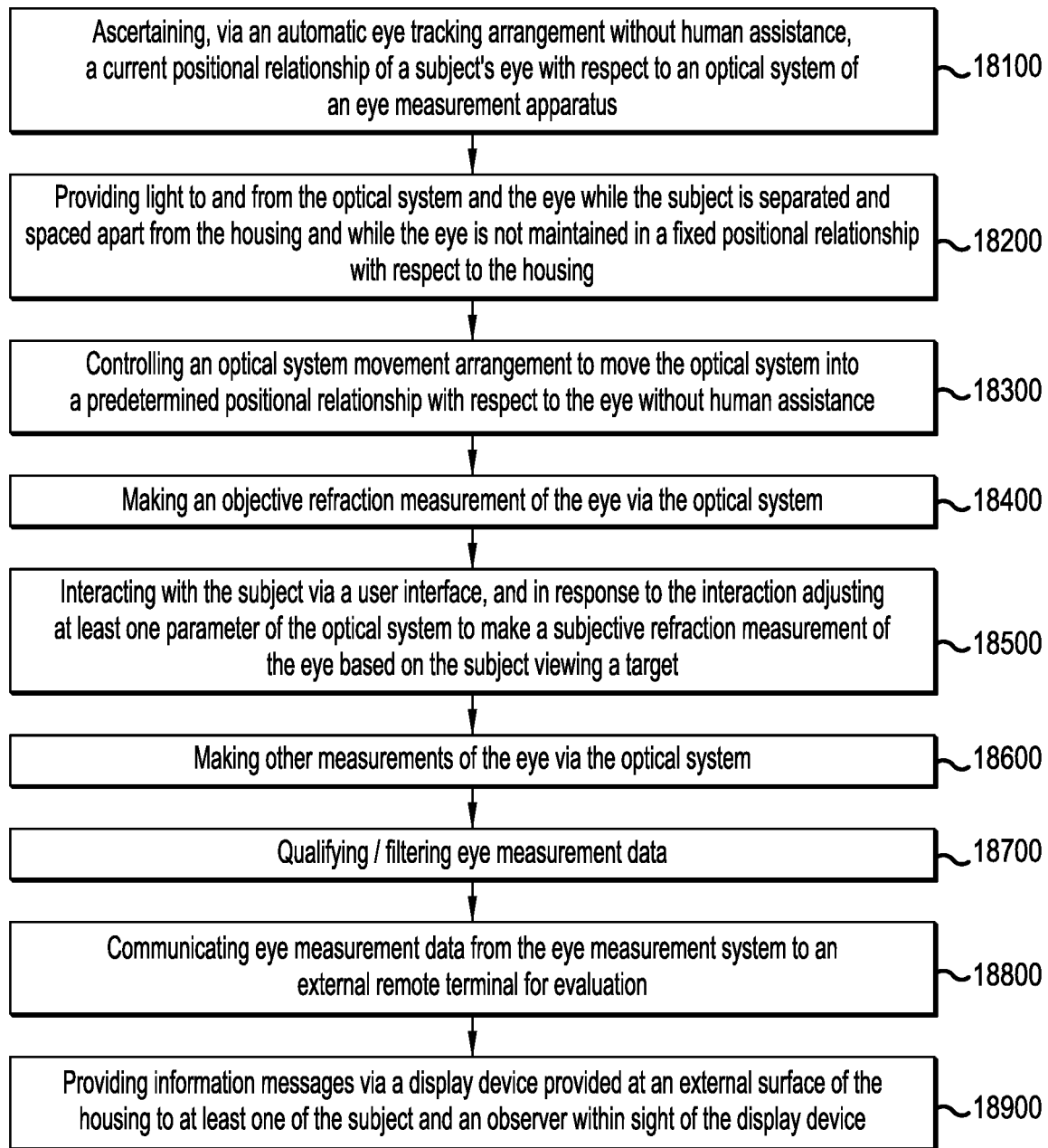
FIG. 18 is a flowchart of an example embodiment of a method of automated non-contact eye examination.

FIG. 18 is a flowchart of an example embodiment of a method 18000 of automated non-contact eye examination.

An operation 18100 includes an eye examination apparatus ascertaining, via an automatic eye tracking arrangement, a current positional relationship of a subject's eye with respect to an optical system of an eye measurement system of the eye examination apparatus. Beneficially, this may be done without human assistance. In some embodiments, operation 18100 may track the positional relationships for both of a subject's eyes at the same time.

An operation 18200 includes the eye examination apparatus providing light to and from the optical system and a subject's eye(s) while the subject is separated and spaced apart from the housing of the eye examination apparatus and while the eye is not maintained in a fixed positional relationship with respect to the housing. In some embodiments, operation 18200 may include providing light to and from the optical system to both of a subject's eyes at the same time. In some embodiments, the eye measurement system may have two separate optical systems for the subject's two eyes, and in that case operation 18200 may include providing light to and from each optical system to a corresponding one of the subject's eyes, for example at the same time.

An operation 18300 includes controlling an optical system movement arrangement of the eye examination apparatus to move the optical system into a predetermined positional relationship with respect to the subject's eye(s). Beneficially, this may be done without human assistance. In some embodiments, the eye examination apparatus may have two separate optical systems for the subject's two eyes, and in that case operation 18300 may include moving each optical system into a predetermined positional relationship with respect to a corresponding one of the subject's eyes.

An operation 18400 includes the eye examination apparatus making an objective refraction measurement of a subject's eye via the optical system. In various embodiments, operation 18400 may include making an objective refraction measurement of a subject's eye via a Shack-Hartmann wavefront detector, a phase diversity sensor, a pyramid sensor, a curvature sensor, a point spread function (PSF) sensor, a retro illumination refractometer, etc. In some embodiments, the eye measurement system may have two separate optical systems and object measurement devices for the subject's two eyes, and in that case operation 18400 may include the eye examination apparatus making an objective refraction measurement of each of the subject's eyes via a corresponding optical system.

An operation 18500 includes the eye examination apparatus interacting with the subject via a user interface, and in response to the interaction adjusting at least one parameter of the optical system to make a subjective refraction measurement of the subject's eye(s) based on the subject viewing a target. Beneficially, the target may be an eye chart. Beneficially, subjective measurements may be made separately for each eye, and a combined subject measurement may be made with the subject viewing the target with both eyes at the same time.

An operation 18600 includes the eye examination apparatus making other measurements and/or examinations of the subject's eye via the optical system, or both eyes in parallel via corresponding optical systems for each eye. In various embodiments, these other measurements and/or examinations may include measuring high order aberrations of the eye, determining intraocular pressure, performing a fundoscopic examination, performing a slit lamp examination, determining keratometry/corneal topography/astigmatism, determining a pupil function, performing confrontation visual field testing (e.g., peripheral vision test), and/or determining extraocular motility. In some embodiments, operation 18600 may be omitted.

An operation 18700 includes the eye examination apparatus qualifying/filtering eye measurement data. In some embodiments, eye measurement data may be filtered to reject at least a portion of the eye measurement data when the portion of the eye measurement data is taken when the automatic eye tracking arrangement has not aligned the optical system to the eye within a specified level of accuracy. In some embodiments, eye measurement data may be filtered to reject at least a portion of the eye measurement data when the portion of the eye measurement data is taken when the images of the eye fail to meet predefined quality criteria due to at least one of: a full blink, a partial blink, an incorrect gaze angle, incomplete dis-accommodation, and a saccade. In some embodiments, operation 18700 may be omitted.

An operation 18800 includes communicating eye measurement data from the eye examination apparatus to an external remote terminal for evaluation, for example by a healthcare professional. The remote terminal may be a computer, a laptop, a tablet device, or even a cell phone. In some embodiments, the external remote terminal may be disposed in a different room than the eye examination apparatus. In some embodiments, the external remote terminal may be disposed in another building, another city, another state/province, or even another country than the eye examination apparatus. In some embodiments, the eye measurement data may be communicated via the Internet. In some embodiments, the eye measurement data may be communicated in real time, as it is processed by the eye examination apparatus. In some embodiments, the eye examination apparatus only communicates filtered eye measurement data which was filtered in operation 18700.

An operation 18900 includes the eye examination apparatus providing information messages via display device 2400 provided at an external surface of the housing to the subject and/or an observer who is within sight of the display device. In some embodiments, such information messages may include advertisements or commercials, which may be in the form of images or video.

In some embodiments, advertisements may be displayed on display device 2440 on an external face of housing 1100 when eye examination apparatus 1000 is not in use. These advertisements can provide information about eye examination apparatus 1000, can provide information about vision health insurance or other public services, or can simply be promotional material from paid sponsors. Furthermore, advertisements can be played on the internal display (see FIG. 22) that is used for the subject visual target at any time during the examination. An example would be right after an objective refraction has been completed so that the refraction results can be used to ensure that the instrument will display the informational content in a clear fashion.

In various embodiments, method 18000 may include additional operations to those shown in FIG. 18. In some embodiments, the eye measurement apparatus may display a QR code (or bar code) with instructions on the video monitor instructing subject 10 to use their camera to sign up for an eye exam. The QR code or hyperlink that connects the potential subject with the instrument (or a network) in order to sign up for and potentially initiate the eye examination.

In some embodiments, when before, during, and/or after a subject encounter with an eye examination apparatus, the subject supplies personal information, including identification information, and may complete a patient intake survey. In some embodiments, this may be accomplished by providing the eye examination apparatus with a webserver which may interact with the subject's mobile phone, tablet or laptop. In some embodiments, a web service accessible via the internet which handles eye examination scheduling may provide these functions, rather than supplying each eye examination apparatus with a webserver.

FIG. 19 illustrates an example of a web page which may be displayed on a subject's cell phone before, during and/or after an interaction with the eye examination apparatus.

Figure 20:
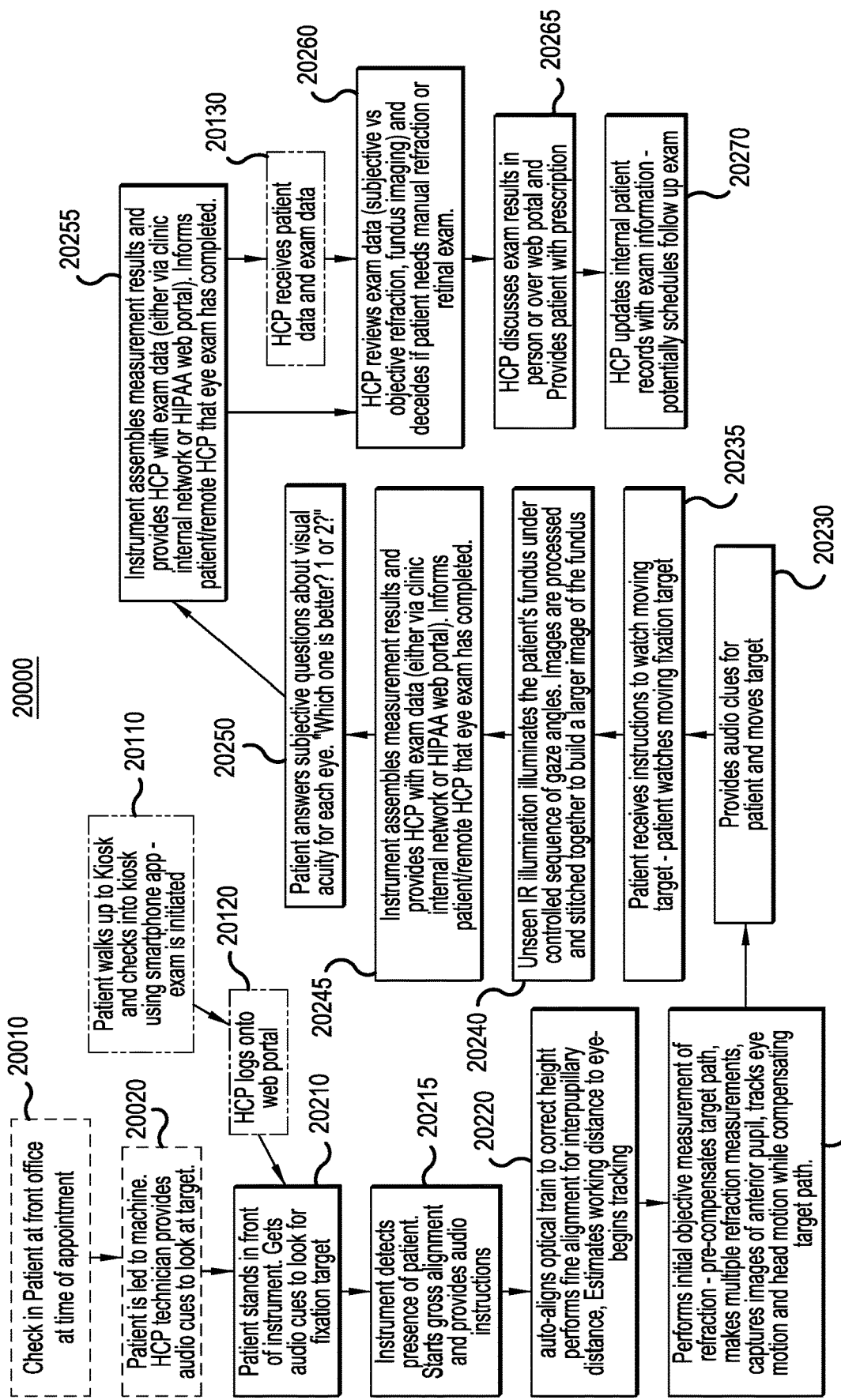
FIG. 20 illustrates an example embodiment for a workflow for an eye examination of an eye.

FIG. 20 illustrates an example embodiment for a workflow 20000 for an eye examination of an eye.

FIG. 20 illustrates operations (20010 and 20020) which occur when the eye examination apparatus is located in an eyecare clinic, operations which occur when the eye examination apparatus is an unattended kiosk (20110, 20120 and 20130), and operations which are common to both situations (all remaining operations).

An operation 20010 includes an eye examination subject, or patient, checking in at the front office of an eye care clinic at the time of appointment.

An operation 20020 includes leading the subject to the eye examination apparatus, and a health care professional (HCP) technician provides audio cues to look at a target in the eye examination apparatus.

An operation 20110 includes an eye examination subject, or patient, walking up to a kiosk comprising an eye examination apparatus and checking in to the kiosk using a smartphone app, and initiating an eye examination.

An operation 20120 includes a HCP logging onto a web portal via an external remote terminal.

An operation 20210 includes the subject standing in front of instrument and receiving audio clues to look for the fixation target.

An operation 20215 includes the eye examination apparatus detecting the presence of the subject, starting gross alignment with the subject's eye(s), and providing audio instructions to the subject.

An operation 20220 includes auto-aligning an optical system to the correct height for the subject, performing fine alignment for interpupillary distance, estimating a working distance to the eye(s), and begin tracking the eye(s).

An operation 20225 includes performing an initial objective measurement of refraction, pre-compensating the target path by correcting for the initially-measured refraction, making multiple refraction measurements of the eye(s), capturing images of the anterior pupil of each eye, and tracking eye motion and head motion while compensating the target path.

An operation 20230 includes providing audio clues for the subject and moving the target.

An operation 20235 includes the subject receiving instructions to watch a moving fixation target, and the subject watching the moving fixation target.

An operation 20240 includes an unseen infrared (IR) illumination illuminating the fundus of the subject's eye(s) under a controlled sequence of gaze angles. Several images of different portions of the fundus may be processed and stitched together to build a larger image of the fundus.

An operation 20245 includes the eye examination apparatus either being controlled by the HCP for a subjective refraction test (e.g., via a tablet device), or running an automated algorithm (kiosk implementation), with the subject responding to standard yes/no questions using voice recognition. Monocular subjective refraction for each eye may be determined.

An operation 20250 includes a subject answering subjective questions about visual acuity for each eye, for example: "Which one is better? 1 or 2?"

An operation 20255 includes the eye examination apparatus assembling eye measurement data or results and providing the assembled eye measurement data/results to the HCP, either via a clinic internal network or HIPAA web portal, and informing a subject and a remote HCP that the eye examination has completed.

An operation 20130 includes the HCP receiving patient data and the assembled eye measurement data/results.

An operation 20260 includes the HCP reviewing the assembled eye measurement data/results (e.g., subjective vs objective refraction, fundus imaging, etc.) and deciding whether the subject needs a manual refraction or retinal examination.

An operation 20265 includes the HCP discussing the eye examination results in person or over a web portal, and providing the subject with a prescription.

An operation 20270 includes the HCP updating internal patient records with information from the eye examination, and potentially scheduling a follow-up eye examination.

Figure 21:
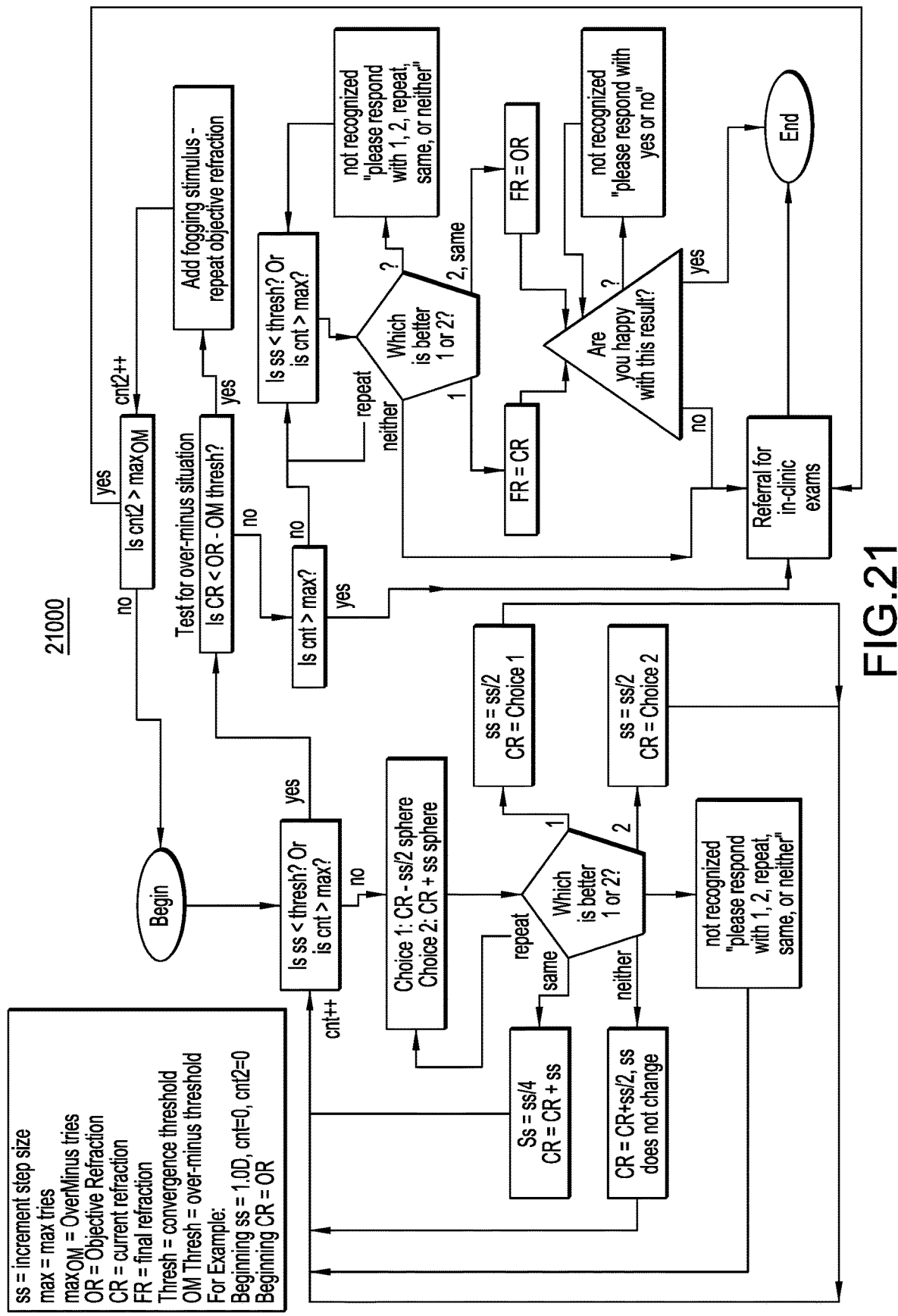
FIG. 21 illustrates an example embodiment for a workflow for an eye examination apparatus to make a subjective (manifest) refraction measurement of an eye.

FIG. 21 illustrates an example embodiment for a workflow 21000 for an eye examination apparatus to make a subjective (manifest) refraction measurement of an eye.

In FIG. 21, the following applies: ss=increment step size; max=max tries; $max_{OM}$=OverMinus tries; OR=Objective Refraction; CR=current refraction; FR=final refraction; Thresh=convergence threshold; OM thresh=over-minus threshold. In an example: beginning ss=1.0 D, cnt=0, cnt2=0 and beginning CR=OR.

Workflow 21000 uses voice recognition and captures subject facial responses during a subjective refraction for post-measurement review by a Health Care Provider (HCP).

The starting point for the subjective examination is after the eye examination apparatus has captured an objective refraction for the eye(s). The objective refraction may be used as the starting point for the subjective refraction measurement. The sphero-cylindrical compensation may be added to the target path (e.g., also accounting for chromatic aberrations and for lane length). Each choice may be briefly presented to the subject, e.g., for 3-5 seconds.

An example in English follow (in some embodiments, other languages may be available).

In this example, the eye examination apparatus gives verbal instructions to the subject (e.g., through a speaker) as follows:

Apparatus: "We will begin a subjective test now—please listen and respond to questions."

Apparatus: "Yes or no—Is the target clear to you now?" If the subject answers no, the eye examination apparatus may reperform the objective refraction measurement or select the most hyperopic objective measurement result. If the subject answers yes, the algorithm proceeds to the next step, and moves on after two additional tries.

Apparatus: "You will now be presented with a choice of targets—please tell the instrument which option is better by answering with one, two, same, neither or repeat. Answer neither if neither choice of targets is clear. Answer same if both choices of targets are clear, and it is difficult to determine which is better. Answer repeat if you would like to see both choices again."

Figure 22:
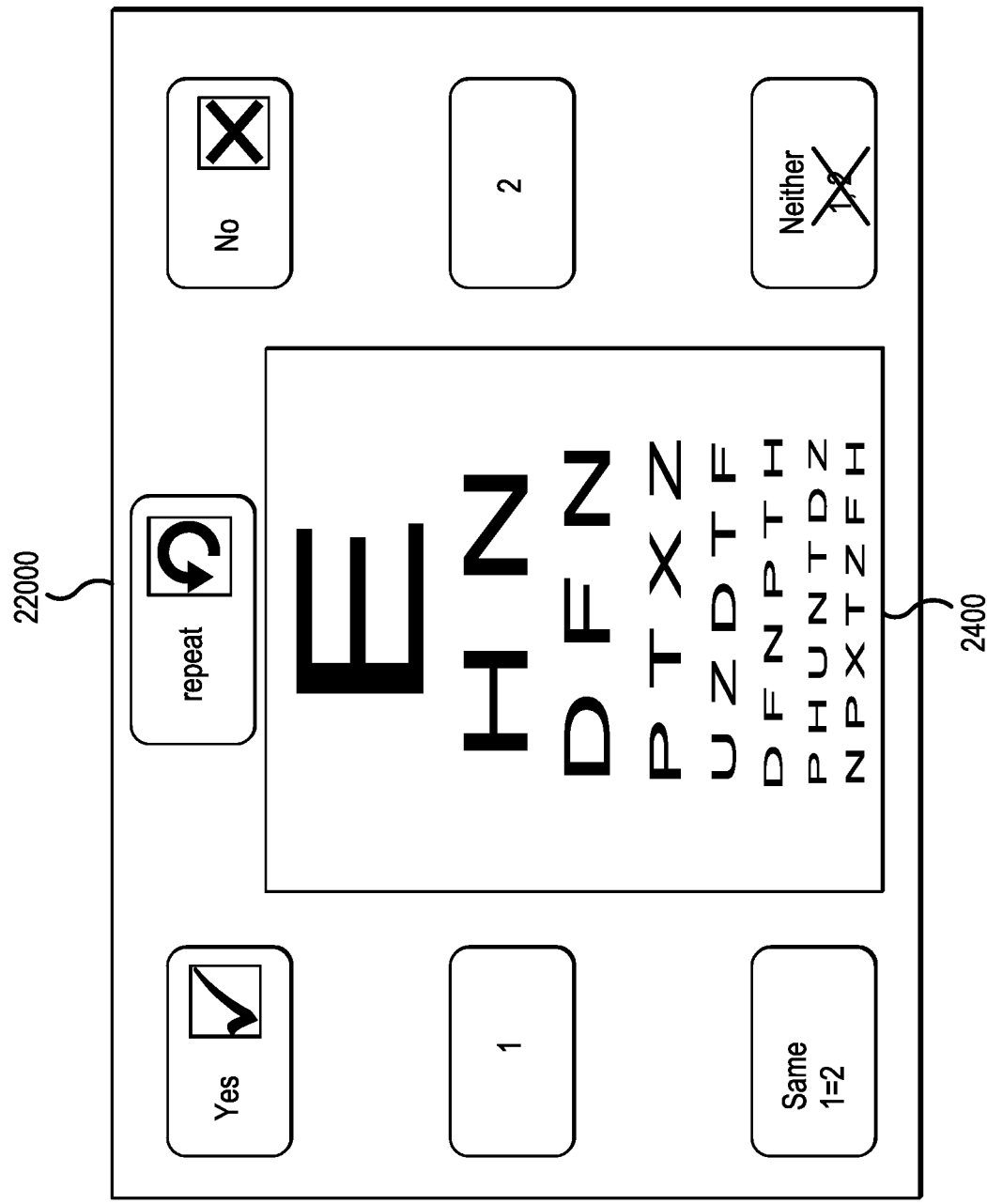
FIG. 22 illustrates an example embodiment of an eye target which may be used to communicate with a subject.

FIG. 22 illustrates an example embodiment of an eye target 22000 which may be used to communicate with a subject.

To further prevent the need for touch screen responses and to assist hearing impaired subjects, messages and possible subject responses can be displayed as words in the subject's preferred language or sign language, or as icons on the target screen. The eye examination apparatus may use voice recognition to determine the subject's response, or the eye examination apparatus may determine the subject's response based upon which of the provided response areas on the display the subject is fixating their eye(s) upon, and/or may interpret sign language or facial expressions to determine subject responses.

As disclosed above, an eye examination apparatus comprising a multi-function ophthalmic instrument for eye health and vision examinations does not require the subject's head to be constrained during examination. It automatically and continuously aligns an internal eye measurement system to the subject's eye(s) during the measurements, regardless of normal subject motion. The optical paths for all measurements include a sufficiently large standoff to allow all measurements to take place with the subject standing comfortably distant from the housing of the instrument, including for example a protective window separating the subject from the measurement module. The eye measurement system is capable of video rate measurements. Audio/visual cues may be provided remotely by the instrument, technician, or physician prior to, during, and after the measurement(s). By incorporating a housing with an easily disinfected smooth outer shell, and by eliminating the traditional headrest and chair, the apparatus can measure subject's eyes without the need for the subject to contact any instrument surfaces or to be in proximity to a technician or HCP during the measurements, thus greatly reducing the risks of cross contamination.

While example embodiments are disclosed herein, one of ordinary skill in the art appreciates that many variations that are in accordance with the present teachings are possible and remain within the scope of the appended claims. The invention therefore is not to be restricted except within the scope of the appended claims.

The invention claimed is:

1. A method, comprising:
    making at least one optical measurement of an eye of a subject with an eye measurement system including an optical system, wherein the eye measurement system is disposed within a housing, wherein the housing is disposed within an examination room, and wherein the housing includes an aperture for providing light to and from the optical system and the eye while the subject is separated and spaced apart from the housing and while the eye is not maintained in a fixed positional relationship with respect to the housing; and
    ascertaining, via an automatic eye tracking arrangement, a current positional relationship of the eye with respect to the optical system, and in response thereto moving the optical system into a predetermined positional relationship with respect to the eye without a presence of an ophthalmic technician in the examination room,
    wherein making the at least one optical measurement of the eye includes:
        making an objective refraction measurement of the eye via the optical system without the presence of the ophthalmic technician in the examination room, and
        interacting with the subject via a user interface and in response to the interaction adjusting at least one parameter of the optical system to make a subjective refraction measurement of the eye, without the presence of the ophthalmic technician in the examination room, based on the subject viewing a target through an optical path which includes a mirror system between the eye and the target for extending a length of the optical path, wherein the optical path further comprises at least one optical element of the optical system.

2. The method of claim 1, wherein the subject does not touch or contact the housing, directly or indirectly.

3. The method of claim 1, wherein the optical system includes a first lens, and wherein the automatic eye tracking arrangement includes a Lidar device which provides light to the eye via the first lens and receives returned light from the eye, wherein the Lidar device determines a distance between the eye and the first lens from the provided light and the returned light.

4. The method of claim 3, wherein the optical system includes a pre-compensation section which brings the target into focus on the subject's eye for making the subjective refraction measurement of the subject's eye, and wherein the distance between the eye and the first lens as determined by the Lidar device is employed to adjust a position of at least one lens in the pre-compensation section to maintain focus and refractive correction for the eye.

5. The method of claim 1, wherein the automatic eye tracking arrangement:
    illuminates the eye;
    receives an image of the eye at a camera;
    outputs image data of the image of the eye from the camera to a processing system; and
    controls an optical system movement arrangement to move the optical system into the predetermined positional relationship with respect to the eye based on the image data.

6. The method of claim 1, wherein the at least one optical measurement of the eye includes at least one of: a high order aberration of the eye, a pupil response characteristic, an external image of the eye, intraocular pressure of the eye, a fundoscope image of the eye, a corneal topography of the eye, an optical coherence tomography of the eye, and a blink rate of the eye.

7. The method of claim 1, further comprising:
    illuminating the eye;
    capturing images of the eye at a camera; and
    presenting to the subject a visual cue for changing a gaze angle of the eye while capturing the images of the eye at the camera.

8. A method, comprising:
making at least one optical measurement of an eye of a subject with an eye measurement system including an optical system, wherein the eye measurement system is disposed within a housing, wherein the housing includes an aperture for providing light to and from the optical system and the eye while the subject is separated and spaced apart from the housing and while the eye is not maintained in a fixed positional relationship with respect to the housing; and
ascertaining, via an automatic eye tracking arrangement, a current positional relationship of the eye with respect to the optical system, and in response thereto moving the optical system into a predetermined positional relationship with respect to the eye,
wherein making the at least one optical measurement of the eye includes:
making an objective refraction measurement of the eye via the optical system, and
interacting with the subject via a user interface and in response to the interaction adjusting at least one parameter of the optical system to make a subjective refraction measurement of the eye based on the subject viewing a target through an optical path which includes a mirror system between the eye and the target for extending a length of the optical path, wherein the optical path further comprises at least one optical element of the optical system;
communicating eye measurement data from an eye measurement apparatus to an external remote terminal for evaluation; and
receiving instructions from the external remote terminal for adjusting at least one operating parameter of the eye measurement system.

9. An apparatus, comprising:
a processing system including a user interface;
an eye measurement system including an optical system, wherein the eye measurement system is configured to make at least one optical measurement of an eye of a subject;
a housing having the eye measurement system disposed therein, wherein the housing includes an aperture for providing light to and from the optical system and the eye while the subject is separated and spaced apart from the housing and while the eye is not maintained in a fixed positional relationship with respect to the housing;
an optical system movement arrangement which is configured to move the optical system; and
an automatic eye tracking arrangement which is configured to ascertain a current positional relationship of the eye with respect to the optical system without a presence of an ophthalmic technician in an examination room where the apparatus is disposed, and in response thereto to control the optical system movement arrangement to move the optical system into a predetermined positional relationship with respect to the eye without a presence of an ophthalmic technician in the examination room,
wherein the eye measurement system includes:
at least one objective refractive measurement device which is configured to make an objective refraction measurement of the eye via the optical system,
a target, and
a mirror system disposed in an optical path between the eye and the target for extending a length of the optical path, wherein the optical path further comprises at least one optical element of the optical system, and
wherein the processing system is configured to interact with the subject via the user interface and in response to the interaction to adjust at least one parameter of the optical system to make a subjective refraction measurement of the eye based on the subject viewing the target.

10. The apparatus of claim 9, wherein the optical system includes a first lens, and wherein the automatic eye tracking arrangement includes a Lidar device which is configured to provide light to the eye via the first lens and to receive returned light from the eye via the first lens for determining a distance between the eye and the first lens.

11. The apparatus of claim 10, wherein the optical system includes a pre-compensation section which is configurable to bring the target into focus on the subject's eye for making the subjective refraction measurement of the subject's eye, and wherein the distance between the eye and the first lens as determined by the Lidar device is employed to adjust a position of at least one lens in the pre-compensation section to maintain focus and refractive correction for the eye.

12. The apparatus of claim 9, including a communication device, wherein the communication device is configured to communicate eye measurement data from the apparatus to an external remote terminal for evaluation.

13. The apparatus of claim 12, wherein the processing system is configured to execute a filtration algorithm for filtering the eye measurement data prior to communication to the external remote terminal to reject at least a portion of the eye measurement data when the portion of the eye measurement data is taken when the automatic eye tracking arrangement has not aligned the optical system to the eye within a specified level of accuracy.

14. The apparatus of claim 12, further comprising:
at least one light source configured to illuminate the eye; and
at least one camera configured to capture images of the eye,
wherein the processing system is configured to execute a filtration algorithm for filtering the eye measurement data prior to communication to the external remote terminal to reject at least a portion of the eye measurement data when the portion of the eye measurement data is taken when the images of the eye fail to meet predefined quality criteria due to at least one of: a full blink, a partial blink, an incorrect gaze angle, incomplete dis-accommodation, and a saccade.

15. The apparatus of claim 9, wherein the optical system includes a pre-compensation section which is configurable to bring the target into focus on the subject's eye for making the subjective refraction measurement of the subject's eye.

16. The apparatus of claim 15, wherein the pre-compensation section comprises one of: a set of discrete lenses, a Badal Optometer, Badal Optometer with Stokes cell, a variable focal length lens, a phase-only spatial light modulator, a deformable mirror and a retroreflection refractometer.

17. The apparatus of claim 16, wherein the pre-compensation section comprises the phase-only spatial light modulator, and wherein the phase-only spatial light modulator is configured to compensate for tilt which is introduced by head and eye motion by the subject.

18. The apparatus of claim 9, wherein the at least one objective refractive measurement device includes one of: a Shack-Hartmann wavefront detector, a phase diversity sensor, a pyramid sensor, a curvature sensor, a point spread function (PSF) sensor, and a retro illumination refractometer.

19. The apparatus of claim 9, wherein the at least one optical measurement of the eye includes at least one of: a high order aberration of the eye, a pupil response characteristic, an external image of the eye, intraocular pressure of the eye, a fundoscope image of the eye, a corneal topography of the eye, an optical coherence tomography of the eye, and a blink rate of the eye.

20. The apparatus of claim 9, further comprising a slit lamp illumination source for enabling a slit lamp examination of the eye.

21. The apparatus of claim 9, wherein the user interface includes at least a microphone for receiving voice communication from the subject, and a speaker for providing audio information to the subject.

22. The apparatus of claim 9, further comprising:
    at least one light source configured to illuminate the eye;
    at least one camera configured to capture images of the eye; and
    a visual cue generator for presenting to the subject a visual cue for changing a gaze angle of the eye while capturing the images of the eye.

23. The apparatus of claim 22, wherein the camera is configured to capture partial fundoscope images of a plurality of different portions of the eye at a corresponding plurality of different gaze angles, and wherein the processing system is configured to stitch together the partial fundoscope images to produce a composite fundoscope image of the eye.

* * * * *